US010551389B2

(12) United States Patent
Manetsch et al.

(10) Patent No.: US 10,551,389 B2
(45) Date of Patent: Feb. 4, 2020

(54) TARGET BINDING MOLECULES IDENTIFIED BY KINETIC TARGET-GUIDED SYNTHESIS

(71) Applicants: UNIVERSITY OF SOUTH FLORIDA, Tampa, FL (US); THE PENN STATE RESEARCH FOUNDATION, University Park, PA (US)

(72) Inventors: Roman Manetsch, Tampa, FL (US); Katya Pavlova Nacheva, Holiday, FL (US); David Lawrence Flanigan, Riverview, FL (US); Niranjan Kumar Namelikonda, Tampa, FL (US); Iredia David Iyamu, Tampa, FL (US); Sameer Shamrao Kulkarni, Ashfield (AU); Megan M. Barber, Parrish, FL (US); Jeremiah Dwayne Tipton, Knoxville, TN (US); Hong-Gang Wang, Palmyra, PA (US); Kenichiro Doi, Hummelstown, PA (US)

(73) Assignees: University of South Florida, Tampa, FL (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 14/889,443

(22) PCT Filed: Aug. 6, 2014

(86) PCT No.: PCT/US2014/049916
§ 371 (c)(1),
(2) Date: Nov. 6, 2015

(87) PCT Pub. No.: WO2015/021134
PCT Pub. Date: Feb. 12, 2015

(65) Prior Publication Data
US 2016/0116482 A1    Apr. 28, 2016

Related U.S. Application Data

(60) Provisional application No. 61/862,826, filed on Aug. 6, 2013.

(51) Int. Cl.
| | | |
|---|---|---|
| *G01N 33/68* | (2006.01) | |
| *H01J 49/00* | (2006.01) | |
| *A61K 31/4418* | (2006.01) | |
| *A61K 31/454* | (2006.01) | |
| *A61K 31/472* | (2006.01) | |
| *A61K 31/4725* | (2006.01) | |
| *A61K 31/495* | (2006.01) | |
| *A61K 31/496* | (2006.01) | |
| *A61K 31/5415* | (2006.01) | |

(52) U.S. Cl.
CPC ..... *G01N 33/6848* (2013.01); *A61K 31/4418* (2013.01); *A61K 31/454* (2013.01); *A61K 31/472* (2013.01); *A61K 31/4725* (2013.01); *A61K 31/495* (2013.01); *A61K 31/496* (2013.01); *A61K 31/5415* (2013.01); *G01N 33/6845* (2013.01); *H01J 49/004* (2013.01); *H01J 49/0036* (2013.01); *G01N 2560/00* (2013.01)

(58) Field of Classification Search
CPC .................................................. G01N 33/6848
USPC ............................................................. 506/9
See application file for complete search history.

(56) References Cited

U.S. PATENT DOCUMENTS

| | | | |
|---|---|---|---|
| 8,524,947 B2 | 9/2013 | Manetsch et al. | |
| 2005/0048567 A1* | 3/2005 | Winchester | G01N 33/58 435/7.1 |
| 2008/0021687 A1* | 1/2008 | Hunter | G06F 19/18 703/11 |
| 2009/0280264 A1* | 11/2009 | Laskin | C07K 17/06 427/474 |
| 2013/0153760 A1* | 6/2013 | Kanie | H01J 49/0031 250/282 |

(Continued)

FOREIGN PATENT DOCUMENTS

| | | |
|---|---|---|
| WO | 2009105746 A2 | 8/2009 |
| WO | 2012021486 | 2/2012 |
| WO | 2012021486 A2 | 2/2012 |

OTHER PUBLICATIONS

Capote et al. (Rapid Communications in Mass Spectrometry, 2007, 21, pp. 1745-1754) (Year: 2007).*

(Continued)

*Primary Examiner* — Karla A Dines
(74) *Attorney, Agent, or Firm* — Thomas|Horstemeyer, LLP

(57) ABSTRACT

Methods of identifying target binding molecules by target guided synthesis are provided. The methods include providing two or more fragments capable of reacting to form the target binding molecule and mixing the fragments with the target. The methods can be used to identify target binding molecules that bind targets such as proteins or nucleic acids, including those that bind shallow binding pockets on the surface of such targets. The methods are applied to the Bcl-XL and Mcl-1 proteins from the Bcl-2 family of proteins. Using thio acid and sulfonyl azide fragments capable of reacting through sulfo-click chemistry, new acyl sulfonamides are identified that bind one or both of the Bcl-XL and Mcl-1 proteins. Pharmaceutical formulations of these target binding molecules are also provided.

6 Claims, 3 Drawing Sheets

(56) References Cited

U.S. PATENT DOCUMENTS

2014/0127734 A1* 5/2014 Charretier .......... G01N 33/6893
435/23
2014/0326875 A1* 11/2014 Asano .................. H01J 49/005
250/288

OTHER PUBLICATIONS

Gergov et al., Journal of Chromatography B, 795, pp. 41-53 (Year: 2003).*
Sameer S. Kulkarni, et al., "Screening of Protein-Protein Interaction Modulators via Sulfo-Click Kinetic Target-Guided Synthesis," ACS Chemical Biology 6:7, Jul. 15, 2011, 724-732.
Xiangdong Hu, et al., "Bcl-X L-Templated Assembly of Its Own Protein-Protein Interaction Modulator from Fragments Decorated with Thio Acids and Sulfonyl Azides," Journal of the American Chemical Society 130:42, Oct. 22, 2008, 13820-13821.
Nacheva, "Development of a Bio-Molecular Fluorescent Probe Used in Kinetic Target-Guided Synthesis for the Identification of Inhibitors of Enzymatic and Protein-Protein Interaction Targets." University of South Florida, Jan. 1, 2012, 1-218.
European Search Report for PCT/US2014049916 dated Oct. 21, 2016. (292103-2281).
Namelikonda, Niranjan Kumar, and Roman Manetsch. "Sulfo-click reaction via in situ generated thioacids and its application in kinetic target-guided synthesis." Chemical Communications 48.10 (2012): 1526-1528.
Arkin, Michelle. "Protein-protein interactions and cancer: small molecules going in for the kill." Current opinion in chemical biology 9.3 (2005): 317-324.
Verdine, Gregory L., and Loren D. Walensky. "The challenge of drugging undruggable targets in cancer: lessons learned from targeting BCL-2 family members." Clinical Cancer Research 13.24 (2007): 7264-7270.
Danial, Nika N., and Stanley J. Korsmeyer. "Cell death: critical control points." Cell 116.2 (2004): 205-219.
Kirkin, Vladimir, Stefan Joos, and Martin Zörnig. "The role of Bcl-2 family members in tumorigenesis." Biochimica et Biophysica Acta (BBA)-Molecular Cell Research 1644.2 (2004): 229-249.
Tse, Christin, et al. "ABT-263: a potent and orally bioavailable Bcl-2 family inhibitor." Cancer research 68.9 (2008): 3421-3428.
Shoemaker, Alex R., et al. "Activity of the Bcl-2 family inhibitor ABT-263 in a panel of small cell lung cancer xenograft models." Clinical Cancer Research 14.11 (2008): 3268-3277.
Shuker, Suzanne B., et al. "Discovering high-affinity ligands for proteins: SAR by NMR." Science 274.5292 (1996): 1531-1534.
Yip, K. W., and J. C. Reed. "Bcl-2 family proteins and cancer." Oncogene 27.50 (2008): 6398-6406.
Vogler, Meike, et al. "Bcl-2 inhibitors: small molecules with a big impact on cancer therapy." Cell Death & Differentiation 16.3 (2009): 360-367.
Willis, Simon N., et al. "Proapoptotic Bak is sequestered by Mcl-1 and Bcl-xL, but not Bcl-2, until displaced by BH3-only proteins." Genes & development 19.11 (2005): 1294-1305.
Nguyen, Mai, et al. "Small molecule obatoclax (GX15-070) antagonizes MCL-1 and overcomes MCL-1-mediated resistance to apoptosis." Proceedings of the National Academy of Sciences 104.49 (2007): 19512-19517.
Konopleva, Marina, et al. "Mechanisms of antileukemic activity of the novel Bcl-2 homology domain-3 mimetic GX15-070 (obatoclax)." Cancer research 68.9 (2008): 3413-3420.
Van Delft, Mark F., et al. "The BH3 mimetic ABT-737 targets selective Bcl-2 proteins and efficiently induces apoptosis via Bak/Bax if Mcl-1 is neutralized." Cancer cell 10.5 (2006): 389-399.
Chen, Shuang, et al. "Mcl-1 down-regulation potentiates ABT-737 lethality by cooperatively inducing Bak activation and Bax translocation." Cancer research 67.2 (2007): 782-791.
Konopleva, Marina, et al. "Mechanisms of apoptosis sensitivity and resistance to the BH3 mimetic ABT-737 in acute myeloid leukemia." Cancer cell 10.5 (2006): 375-388.
Lin, Xiaoyu, et al. "'Seed'analysis of off-target siRNAs reveals an essential role of Mcl-1 in resistance to the small-molecule Bcl-2/Bcl-XL inhibitor ABT-737." Oncogene 26.27 (2007): 3972-3979.
Tahir, Stephen K., et al. "Influence of Bcl-2 family members on the cellular response of small-cell lung cancer cell lines to ABT-737." Cancer research 67.3 (2007): 1176-1183.
Woods, Nicholas T., et al. "Anoikis, initiated by Mcl-1 degradation and Bim induction, is deregulated during oncogenesis." Cancer research 67.22 (2007): 10744-10752.
Yecies, Derek, et al. "Acquired resistance to ABT-737 in lymphoma cells that up-regulate MCL-1 and BFL-1." Blood 115.16 (2010): 3304-3313.
Erlanson, Daniel A. "Fragment-based lead discovery: a chemical update." Current opinion in biotechnology 17.6 (2006): 643-652.
Carr, Robin AE, et al. "Fragment-based lead discovery: leads by design." Drug discovery today 10.14 (2005): 987-992.
Poulsen, Sally-Ann, and Laurent F. Bornaghi. "Fragment-based drug discovery of carbonic anhydrase II inhibitors by dynamic combinatorial chemistry utilizing alkene cross metathesis." Bioorganic & medicinal chemistry 14.10 (2006): 3275-3284.
Congreve, Miles, et al. "Recent developments in fragment-based drug discovery." Journal of medicinal chemistry 51.13 (2008): 3661-3680.
Jencks, William P. "On the attribution and additivity of binding energies." Proceedings of the National Academy of Sciences 78.7 (1981): 4046-4050.
Hu, Xiangdong, et al. "Bcl-XL-Templated Assembly of Its Own Protein-Protein Interaction Modulator from Fragments Decorated with Thio Acids and Sulfonyl Azides." Journal of the American Chemical Society 130.42 (2008): 13820-13821.
Manetsch, Roman, et al. "In situ click chemistry: enzyme inhibitors made to their own specifications." Journal of the American Chemical Society 126.40 (2004): 12809-12818.
Yamaguchi, Hirohito, and Hong-Gang Wang. "Bcl-XL protects BimEL-induced Bax conformational change and cytochrome C release independent of interacting with Bax or BimEL." Journal of Biological Chemistry 277.44 (2002): 41604-41612.
Hirose, Tomoyasu, et al. "Chitinase inhibitors: extraction of the active framework from natural argifin and use of in situ click chemistry." The Journal of antibiotics 62.5 (2009): 277-282.
Agnew, Heather D., et al. "Iterative In Situ Click Chemistry Creates Antibody-like Protein-Capture Agents." Angewandte Chemie International Edition 48.27 (2009): 4944-4948.
Wang, et al. "An integrated microfluidic device for large-scale in situ click chemistry screening." Lab on a Chip 9.16 (2009): 2281-2285.
Carrillo, Nancy, et al. "Iterative, aqueous synthesis of β3-oligopeptides without coupling reagents." Journal of the American Chemical Society 128.5 (2006): 1452-1453.
Bode, Jeffrey W., Ryan M. Fox, and Kyle D. Baucom. "Chemoselective Amide Ligations by Decarboxylative Condensations of N-Alkylhydroxylamines and α-Ketoacids." Angewandte Chemie International Edition 45.8 (2006): 1248-1252.
Ryadnov, Maxim G., and Derek N. Woolfson. "Self-assembled templates for polypeptide synthesis." Journal of the American Chemical Society 129.45 (2007): 14074-14081.
Park, Cheol-Min, et al. "Design, synthesis, and computational studies of inhibitors of Bcl-XL." Journal of the American Chemical Society 128.50 (2006): 16206-16212.
Yin, Hang, et al. "Terephthalamide derivatives as mimetics of helical peptides: disruption of the Bcl-xL/Bak interaction." Journal of the American Chemical Society 127.15 (2005): 5463-5468.
Yin, Hang, et al. "Terphenyl-based Bak BH3 α-helical proteomimetics as low-molecular-weight antagonists of Bcl-xL." Journal of the American Chemical Society 127.29 (2005): 10191-10196.
Kutzki, Olaf, et al. "Development of a potent Bcl-xL antagonist based on α-helix mimicry." Journal of the American Chemical Society 124.40 (2002): 11838-11839.

(56) References Cited

OTHER PUBLICATIONS

Tang, Guozhi, et al. "Pyrogallol-based molecules as potent inhibitors of the antiapoptotic Bcl-2 proteins." Journal of medicinal chemistry 50.8 (2007): 1723-1726.
Park, Cheol-Min, et al. "Discovery of an orally bioavailable small molecule inhibitor of prosurvival B-cell lymphoma 2 proteins." Journal of medicinal chemistry 51.21 (2008): 6902-6915.
Takahashi, Yoshinori, et al. "Loss of Bif-1 suppresses Bax/Bak conformational change and mitochondrial apoptosis." Molecular and cellular biology 25.21 (2005): 9369-9382.
Kellenberger, Esther, et al. "Comparative evaluation of eight docking tools for docking and virtual screening accuracy." Proteins: Structure, Function, and Bioinformatics 57.2 (2004): 225-242.
Arkin, Michelle R., and James A. Wells. "Small-molecule inhibitors of protein-protein interactions: progressing towards the dream." Nature reviews Drug discovery 3.4 (2004): 301-317.
Berg, Thorsten. "Modulation of protein-protein interactions with small organic molecules." Angewandte Chemie International Edition 42.22 (2003): 2462-2481.
Cancilla, Mark T., and Daniel A. Erlanson. "Tethering: Fragment-Based Drug Discovery by Mass Spectrometry." Mass Spectrometry in Medicinal Chemistry: Applications in Drug Discovery (2007): 303-320.
Hu, Xiangdong, and Roman Manetsch. "Kinetic target-guided synthesis." Chemical Society Reviews 39.4 (2010): 1316-1324.
Vajda, S. and F. Guarnieri, Characterization of protein-ligand interaction sites using experimental and computational methods. Current Opinion in Drug Discovery & Development, 2006. 9(3): p. 354-362.
Crich, D. and K. Sasaki, Reaction of Thioacids with Isocyanates and Isothiocyanates: A Convenient Amide Ligation Process. Organic Letters, 2009. 11(15): p. 3514-3517.
Bemis, Guy W., and Mark A. Murcko. "Properties of known drugs. 2. Side chains." Journal of medicinal chemistry 42.25 (1999): 5095-5099.
Beroukhim, Rameen, et al. "The landscape of somatic copy-number alteration across human cancers." Nature 463.7283 (2010): 899-905.
Ghose, Arup K., Vellarkad N. Viswanadhan, and John J. Wendoloski. "A knowledge-based approach in designing combinatorial or medicinal chemistry libraries for drug discovery. 1. A qualitative and quantitative characterization of known drug databases." Journal of combinatorial chemistry 1.1 (1999): 55-68.
Kolakowski, Robert V., et al. "Mechanism of thio acid/azide amidation." Journal of the American Chemical Society 128.17 (2006): 5695-5702.
Bemis, Guy W., and Mark A. Murcko. "The properties of known drugs. 1. Molecular frameworks." Journal of medicinal chemistry 39.15 (1996): 2887-2893.
Bohacek, Regine S., Colin McMartin, and Wayne C. Guida. "The art and practice of structure-based drug design: A molecular modeling perspective." Medicinal research reviews 16.1 (1996): 3-50.
Hajduk, Philip J. "Fragment-based drug design: how big is too big?." Journal of medicinal chemistry 49.24 (2006): 6972-6976.
Krasinski, Antoni, et al. "In situ selection of lead compounds by click chemistry: target-guided optimization of acetylcholinesterase inhibitors." Journal of the American Chemical Society 127.18 (2005): 6686-6692.
Mamidyala, Sreeman K., and M. G. Finn. "In situ click chemistry: probing the binding landscapes of biological molecules." Chemical Society Reviews 39.4 (2010): 1252-1261.
Nguyen, Régis, and Ivan Huc. "Using an enzyme's active site to template inhibitors." Angewandte Chemie International Edition 40.9 (2001): 1774-1776.
Reed, John C., et al. "BCL-2 family proteins: Regulators of cell death involved in the pathogenesis of cancer and resistance to therapy." Journal of cellular biochemistry 60.1 (1996): 23-32.

Schulz, Michèle N., and Roderick E. Hubbard. "Recent progress in fragment-based lead discovery." Current opinion in pharmacology 9.5 (2009): 615-621.
Wells, James A., and Christopher L. McClendon. "Reaching for high-hanging fruit in drug discovery at protein-protein interfaces." Nature 450.7172 (2007): 1001-1009.
Whiting, Matthew, et al. "Inhibitors of HIV-1 Protease by Using In Situ Click Chemistry." Angewandte Chemie International Edition 45.9 (2006): 1435-1439.
Mocharla, Vani P., et al. "In Situ Click Chemistry: Enzyme-Generated Inhibitors of Carbonic Anhydrase II." Angewandte Chemie International Edition 44.1 (2005): 116-120.
Oltersdorf, Tilman, et al. "An inhibitor of Bcl-2 family proteins induces regression of solid tumours." Nature 435.7042 (2005): 677-681.
Reed, John C. "Bcl-2 family proteins: strategies for overcoming chemoresistance in cancer." Advances in pharmacology (San Diego, Calif.) 41 (1997): 501.
Shangguan, Ning, et al. "The reaction of thio acids with azides: A new mechanism and new synthetic applications." Journal of the American Chemical Society 125.26 (2003): 7754-7755.
Murray, Christopher W., and David C. Rees. "The rise of fragment-based drug discovery." Nature chemistry 1.3 (2009): 187-192.
Petros, Andrew M., et al. "Discovery of a potent inhibitor of the antiapoptotic protein Bcl-xL from NMR and parallel synthesis." Journal of medicinal chemistry 49.2 (2006): 656-663.
Sasaki, Tadashi, et al. "Synthesis of adamantane derivatives. 52. 1, 3-Dipolar cycloaddition reactions of 1-azidoadamantane. Reactivity, regioselectivity, and carbon-13 nuclear magnetic resonance spectra of 1-(1-adamantyl)-. DELTA. 2-1, 2, 3-triazolines and-1H-1, 2, 3-triazoles." The Journal of Organic Chemistry 46.9 (1981): 1800-1804.
Wang, Jinyi, et al. "Integrated microfluidics for parallel screening of an in situ click chemistry library." Angewandte Chemie 118.32 (2006): 5402-5407.
Wendt, Michael D., et al. "Discovery and structure-activity relationship of antagonists of B-cell lymphoma 2 family proteins with chemopotentiation activity in vitro and in vivo." Journal of medicinal chemistry 49.3 (2006): 1165-1181.
Huth, Jeffrey R., and Chaohong Sun. "Utility of NMR in lead optimization: fragment-based approaches." Combinatorial chemistry & high throughput screening 5.8 (2002): 631-643.
Roque, Dario R., et al. "Synthesis of 1, 2, 3-triazoles by cycloadditions of azides with enol ethers." Synthesis 15 (2005): 2497-2502.
Pellecchia, Maurizio, and John C. Reed. "Inhibition of Anti-Apoptotic Bcl-2 Family Proteins by Natural Polyphenols New Avenues for Cancer Chemoprevention and Chemotherapy." Current pharmaceutical design 10.12 (2004): 1387-1398.
Balani, Suresh K., et al. "Strategy of utilizing in vitro and in vivo ADME tools for lead optimization and drug candidate selection." Current topics in medicinal chemistry 5.11 (2005): 1033-1038.
Sharpless, K. Barry, and Roman Manetsch. "In situ click chemistry: a powerful means for lead discovery." (2006): 525-538.
Nacheva et al. Development of a Bio-Molecular Fluorescent Probe Used in Kinetic Target-Guided Synthesis for the Identification of Inhibitors of Enzymatic and Protein-Protein Interaction Targets. Ph. D. dissertation University of South Florida, Tampa, FL Jan. 2012. Available on the internet: <URL: scholarcommons.usf.edu/cgi/viewcontent.cgi?article=5572&context=etd>. Especially p. 20 para 1, p. 38 fig 1.15, p. 146 fig 4.1, p. 147 para 2, p. 150 para 2, p. 157 para 1, p. 158 fig 4.7.
Kulkarni et al. Screening of protein-protein interaction modulators via sulfo-click kinetic target-guided synthesis. ACS Chem Biol Jul. 15, 2011 vol. 6 No. 7 pp. 724-732. Especially abstract, p. 728 fig 4).
International Search Report and Written Opinion dated Jan. 23, 2015.

\* cited by examiner

Figure 1. Schematic representation of mass spectrometry analysis with different single and triple quadrupole scanning modes: A) a full scan with MS, B) Selected Ion Mode (SIM), C) Multiple Reaction Monitoring (MRM).

Figure 2. Schematic representation of Multiple Reaction Monitoring (MRM) mode of analysis performed with a triple quadrupole mass spectrometer

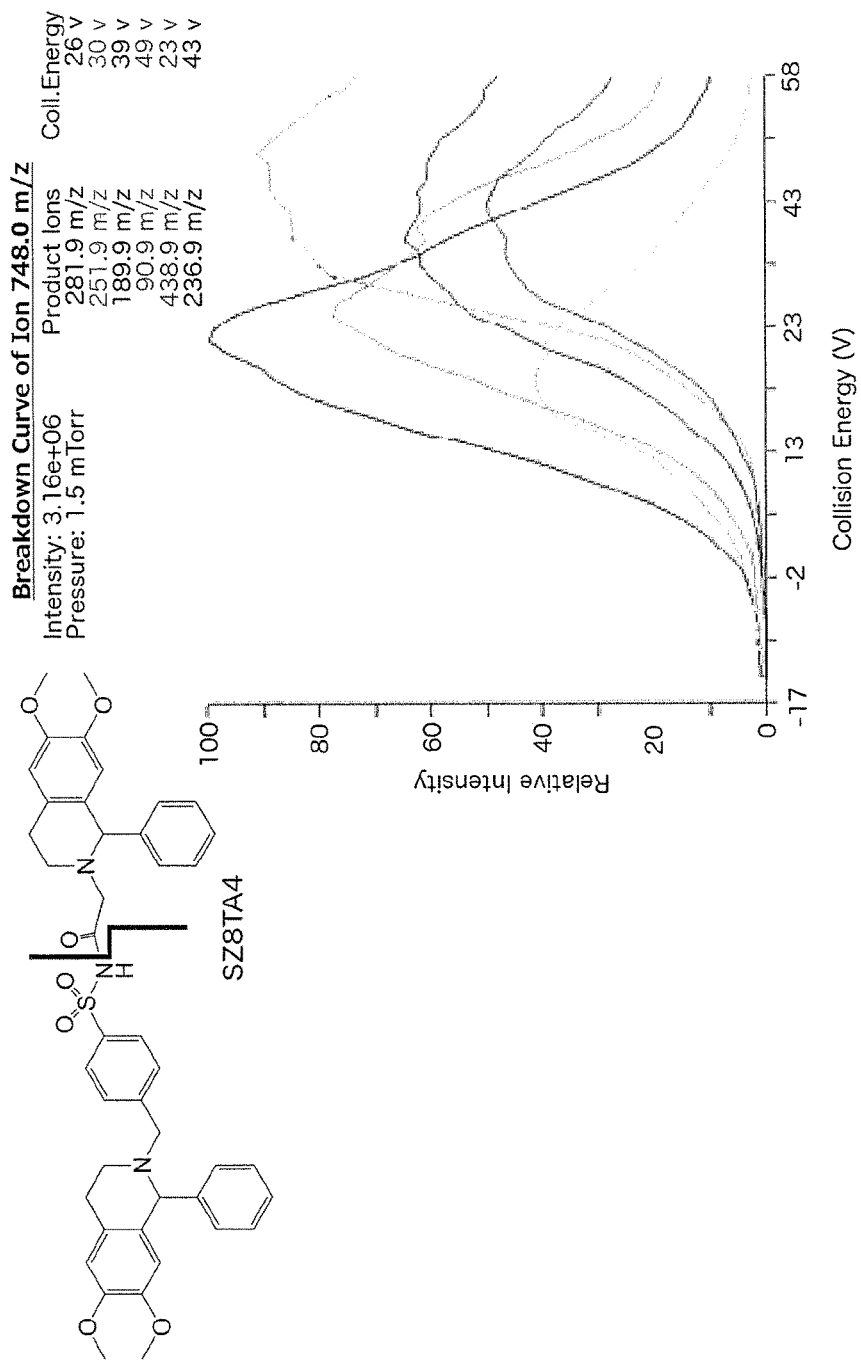

Figure 3. Collision-activated defragmentation curve of acylsulfonamide SZ8TA4. Note, of all possible fragmentation pathways, the one leading to an acylium ion has the highest relative ion abundance and requires the least collision energy (among the most abundant ions). The relative abundance of each ion represents the number of times an ion of that m/z ratio strikes the detector.

FIG. 3

TARGET BINDING MOLECULES IDENTIFIED BY KINETIC TARGET-GUIDED SYNTHESIS

CROSS-REFERENCE TO RELATED APPLICATIONS

This application is the 35 U.S.C. § 371 national stage of, and claims priority to and the benefit of, PCT application PCT/US2014/049916, filed Aug. 6, 2014, which claims priority to and the benefit of U.S. Provisional Application No. 61/862,826 filed Aug. 6, 2013, the disclosure of each which is herein incorporated by reference in their entirety.

FIELD OF THE DISCLOSURE

The disclosure is generally in the field of kinetic target guided synthesis, in particular kinetic target guided synthesis of compounds that modulate protein-protein interactions, and uses thereof.

BACKGROUND OF THE DISCLOSURE

Protein-protein interactions are central to many biological processes and hence represent a large and important class of targets for human therapeutics (Arkin et al., *Nature Reviews Drug Discovery*, 2004. 3(4):301-317; Berg, *Angewandte Chemie-International Edition*, 2003. 42(22):2462-2481). Recent discovery of a variety of low-molecular-weight compounds that interfere with biologically relevant protein-protein complexes has fostered the identification and validation of new therapy strategies for a variety of diseases (Arkin, *Current Opinion in Chemical Biology*, 2005. 9(3): 317-324). Nevertheless, disrupting or modulating protein-protein interactions (PPIs) with low-molecular-weight compounds is extremely difficult due to the lack of deep binding pockets on protein surfaces. The adaptive nature of binding sites on protein surfaces creates additional challenges for lead compound design. Furthermore, because PPIs occur over a large surface area, it is difficult to identify potent and specific Protein-Protein Interaction Modulators (PPIMs) by conventional high throughput screening (HTS) of small molecule libraries.

Over the past 15 years, a variety of fragment-based lead discovery approaches have been developed and successfully applied for the development of potent PPIMs. [Albert et al., *Current Topics in Medicinal Chemistry*, 2007, 7(16):1600-1629; Erlanson, *Current Opinion in Biotechnology*, 2006. 17(6):643-652; Carr et al., *Drug Discovery Today*, 2005. 10(14):987-99]. These approaches are commonly based on the detection of fragments binding to the target protein followed by the study of their binding to the protein target at atomic level resolution using X-ray crystallography or NMR spectroscopy. The initial hits are further optimized via fragment growing, in which fragments are extended into identified binding sites step-by-step, or via fragment linking, in which fragments identified to bind to adjacent binding sites are covalently linked together. (Poulsen et al., *Bioorganic & Medicinal Chemistry*, 2006. 14(10):3275-3284; Schulz et al., *Current Opinion in Pharmacology*, 2009. 9(5):615-621; Congreve et al., *Journal of Medicinal Chemistry*, 2008. 51(13):3661-3680).

Even though fragment-based discovery strategies have been very successful for the development of PPIMs, they are mainly limited by two constraints. Detection and quantification of fragment binding requires specially designed methodology due to the weak binding typically observed for fragments. Furthermore, the optimization of fragments into potent and selective compounds is not straightforward and not rapidly achievable, even though structural information is available. (Schulz et al., *Current opinion in pharmacology*, 2009. 9(5):615-21; Murray et al., *Nature Chemistry*, 2009. 1(3):187-192). For example, though good quality NMR structures were available, the well-known development of Bcl-XL PPIMs by Abbott required several design iterations and the preparation and testing of more than thousand compounds in order to yield ABT-737 (Oltersdorf, et al., *Nature*, 2005. 435(7042):677-681; Wendt, et al., *Journal of Medicinal Chemistry*, 2006. 49(3):1165-1181; Hajduk, *Journal of Medicinal Chemistry*, 2006. 49(24): 6972-6976). Furthermore, of the very first design consisting of 21 different compounds containing the structural motifs of the initial fragments identified by NMR, most compounds bound to Bcl-XL with a dissociation constant greater than 10 mM. (Petros, et al., *Journal of Medicinal Chemistry*, 2006. 49(2):656-663).

Recently, fragment-based discovery strategies have been reported which involve the protein target directly to select and assemble its own inhibitory compounds from pools of reactive fragments. These approaches, also termed in situ click chemistry or kinetic TGS approaches, were conceptually described in detail in the 1980s and are still relatively unexplored compared to dynamic combinatorial chemistry (Sharpless et al., *Expert Opin. Drug Discovery*, 2006. 1(6): 525-538; Hu et al., *Chemical Society Reviews*, 2010. 39(4): 1316-1324; Jencks, *Proceedings of the National Academy of Sciences of the United States of America-Biological Sciences*, 1981. 78(7): 4046-4050). Thus far kinetic TGS has mainly been applied to the identification of potent enzyme inhibitors, nevertheless kinetic TGS offers an attractive approach to PPIM lead discovery because it allows the protein to select and combine building blocks that fit best into its binding sites, thus assembling larger compounds (Sharpless et al., *Expert Opin. Drug Discovery*, 2006. 1(6): 525-538; Hu et al., *Chemical Society Reviews*, 2010. 39(4): 1316-1324). The screening method can be as simple as determining whether or not the PPIM product has been formed in a given test mixture. Additionally, if one considers a protein target to be an ensemble of interconverting conformers, it is easy to imagine this protein undergoing dynamic motion to repeatedly expose unique structural elements vulnerable to strong binding by the right inhibitor. Unfortunately, such short-lived targets of opportunity cannot be "seen" or easily discovered with present techniques.

SUMMARY OF THE DISCLOSURE

Methods of identifying target binding molecules by target guided synthesis are provided. The methods include providing two or more fragments capable of reacting to form the target binding molecule and mixing the fragments with the target. The methods can be used to identify target binding molecules that bind targets such as proteins or nucleic acids, including those that bind shallow binding pockets on the surface of such targets. The methods are applied to the Bcl-XL and Mcl-1 proteins from the Bcl-2 family of proteins. Using thio acid and sulfonyl azide fragments capable of reacting through sulfo-click chemistry, new acyl sulfonamides are identified that bind one or both of the Bcl-XL and Mcl-1 proteins. Compositions and pharmaceutical formulations of these target binding molecules are also provided.

Methods of identifying target binding molecules using kinetic target guided synthesis are provided. The methods can include providing a plurality of first fragments and a plurality of second fragments capable of reacting to form a target binding molecule, mixing the fragments with the target under conditions where the fragments can react, and analyzing the mixture to identify target binding molecules. The plurality of first fragments can have a first reactive functional group and the plurality of second fragments can have a second reactive functional group capable of forming a covalent bond with the first reactive functional group of the first fragments. The number of fragment combinations can be greater than 200, 500, or even greater than 1,000. For example, the number from fragment combinations can be about 200-10,000.

The methods can include analyzing the mixture with a tandem mass spectrometer to identify a mass spectrometer-mediated fragmentation product and identify the target binding molecule(s) corresponding to the fragmentation product. The tandem mass spectrometer can be a QqTOF mass spectrometer, triple quadrupole mass spectrometer, ion trap mass spectrometer, ion trap time-of-flight (TOF) mass spectrometer, ion cyclotron resonance (ICR) mass spectrometer, time-of-flight time-of-flight (TOF-TOF) mass spectrometer, Fourier transform ion cyclotron resonance mass spectrometer, electric sector-magnetic sector mass spectrometer, magnetic sector-electric sector mass spectrometer, or electric sector-electric sector mass spectrometer among others. In some embodiments the analyzing step uses multiple reaction monitoring of the fragmentation product to identify the target binding molecule(s) corresponding to the fragmentation product.

The fragments can be small molecules. One or more of the fragments can be a polypeptide or polynucleotide fragment. The fragments can include reactive functional groups capable of forming a covalent bond. The plurality of first fragments can have a first reactive functional group and the plurality of second fragments can have a second reactive functional group capable of forming a covalent bond with the first reactive functional group of the first fragments. The first reactive functional group can be a primary amine, wherein the second reactive functional group can be an isothiocyanate, isocyanate, acyl azide, NHS ester, sulfonyl chloride, aldehyde, glyoxal, epoxide, oxirane, carbonate, aryl halide, imidoester, carbodiimide, anhydride, or fluorophenyl ester. The first reactive functional group can be a thiol group, wherein the second reactive functional group can be a maleimide, haloacetyl, or pyridyl disulfide. The first reactive functional group can be a thioacid group and the second reactive functional group can be a sulfonyl azide. In some embodiments, the first fragments are thioacids, the second fragments are sulfonyl azides, the target binding molecule(s) are acylsulfonamides, and the fragmentation product is an acylium ion fragmentation product.

The methods can be used to identify target binding molecules that can bind a variety of targets. In some embodiments the target is a polypeptide or a polynucleotide. For example, the target can be a Bcl-2 family protein. The target can be Bcl-2, Bcl-XL, Mcl-1, Mcl-2, A1/BFL-1, Boo/Diva, Bcl-w, Bcl-y, Bak, Bax, Bad, tBid, Harakiri, Bim, Bcl-Xs, Bmf, Egl-1, Puma, or Noxa.

The methods are used to identify target binding molecules. In particular, the methods are used herein to identify acylsulfonamides. The acylsulfonamides can bind to or inhibit protein-protein interactions in Bcl-2, Bcl-XL, or Mcl-1. The target binding molecules can include acylsulfonamides identified herein as SZ10TA15, SZ10TA2, SZ10TA20, SZ10TA21, SZ10TA25, SZ10TA34, SZ10TA40, SZ10TA41, SZ10TA44, SZ11TA25, SZ11TA30, SZ11TA40, SZ12TA2, SZ12TA23, SZ12TA42, SZ14TA40, SZ14TA42, SZ15TA1, SZ15TA14, SZ15TA15, SZ15TA17, SZ15TA24, SZ15TA25, SZ15TA3, SZ15TA34, SZ15TA5, SZ15TA7, SZ15TA8, SZ16TA21, SZ16TA44, SZ17TA14, SZ17TA15, SZ17TA17, SZ17TA20, SZ17TA24, SZ17TA25, SZ17TA3, SZ17TA30, SZ17TA40, SZ17TA45, SZ17TA7, SZ17TA8, SZ1TA14, SZ1TA23, SZ1TA30, SZ21TA23, SZ23TA2, SZ24TA30, SZ27TA42, SZ28TA30, SZ28TA31, SZ28TA45, SZ2TA31, SZ31TA14, SZ31TA15, SZ31TA17, SZ31TA24, SZ31TA3, SZ31TA30, SZ31TA31, SZ31TA40, SZ31TA44, SZ31TA45, SZ31TA8, SZ32TA42, SZ34TA42, SZ35TA17, SZ35TA24, SZ35TA3, SZ35TA7, SZ36TA2, SZ37TA42, SZ4TA17, SZ4TA21, SZ4TA30, SZ6TA23, SZ7TA2, SZ7TA23, SZ7TA45, SZ8TA14, SZ8TA2, SZ8TA20, SZ8TA24, SZ8TA31, SZ9TA1, SZ9TA14, SZ9TA17, SZ9TA20, SZ9TA25, SZ9TA3, SZ9TA5, or SZ9TA7.

Compositions and pharmaceutical formulations containing a target binding molecule are provided herein. In some embodiments, pharmaceutical formulations are provided containing a therapeutically effective amount of an acylsulfonamide identified herein as binding to or inhibiting protein-protein interactions in Bcl-2, Bcl-XL, or Mcl-1. Pharmaceutical formulations can include a therapeutically effective amount of one or more acylsulfonamides identified herein as SZ10TA15, SZ10TA2, SZ10TA20, SZ10TA21, SZ10TA25, SZ10TA34, SZ10TA40, SZ10TA41, SZ10TA44, SZ11TA25, SZ11TA30, SZ11TA40, SZ12TA2, SZ12TA23, SZ12TA42, SZ14TA40, SZ14TA42, SZ15TA1, SZ15TA14, SZ15TA15, SZ15TA17, SZ15TA24, SZ15TA25, SZ15TA3, SZ15TA34, SZ15TA5, SZ15TA7, SZ15TA8, SZ16TA21, SZ16TA44, SZ17TA14, SZ17TA15, SZ17TA17, SZ17TA20, SZ17TA24, SZ17TA25, SZ17TA3, SZ17TA30, SZ17TA40, SZ17TA45, SZ17TA7, SZ17TA8, SZ1TA14, SZ1TA23, SZ1TA30, SZ21TA23, SZ23TA2, SZ24TA30, SZ27TA42, SZ28TA30, SZ28TA31, SZ28TA45, SZ2TA31, SZ31TA14, SZ31TA15, SZ31TA17, SZ31TA24, SZ31TA3, SZ31TA30, SZ31TA31, SZ31TA40, SZ31TA44, SZ31TA45, SZ31TA8, SZ32TA42, SZ34TA42, SZ35TA17, SZ35TA24, SZ35TA3, SZ35TA7, SZ36TA2, SZ37TA42, SZ4TA17, SZ4TA21, SZ4TA30, SZ6TA23, SZ7TA2, SZ7TA23, SZ7TA45, SZ8TA14, SZ8TA2, SZ8TA20, SZ8TA24, SZ8TA31, SZ9TA1, SZ9TA14, SZ9TA17, SZ9TA20, SZ9TA25, SZ9TA3, SZ9TA5, or SZ9TA7.

Methods of using the pharmaceutical formulations are provided. The methods can include administering a formulation provided herein to a subject to inhibit protein-protein interactions of a Bcl-2 family protein and/or to treat or prevent cancer, for example.

BRIEF DESCRIPTION OF THE DRAWINGS

FIG. 3 is a graph showing a collision-activated defragmentation curve of acylsulfonamide SZ8TA4. (Note, of all possible fragmentation pathways, the one leading to an acylium ion has the highest relative ion abundance and requires the least collision energy (among the most abundant ions). The relative abundance of each ion represents the number of times an ion of that m/z ratio strikes the detector.)

DETAILED DESCRIPTION

Figure 1:
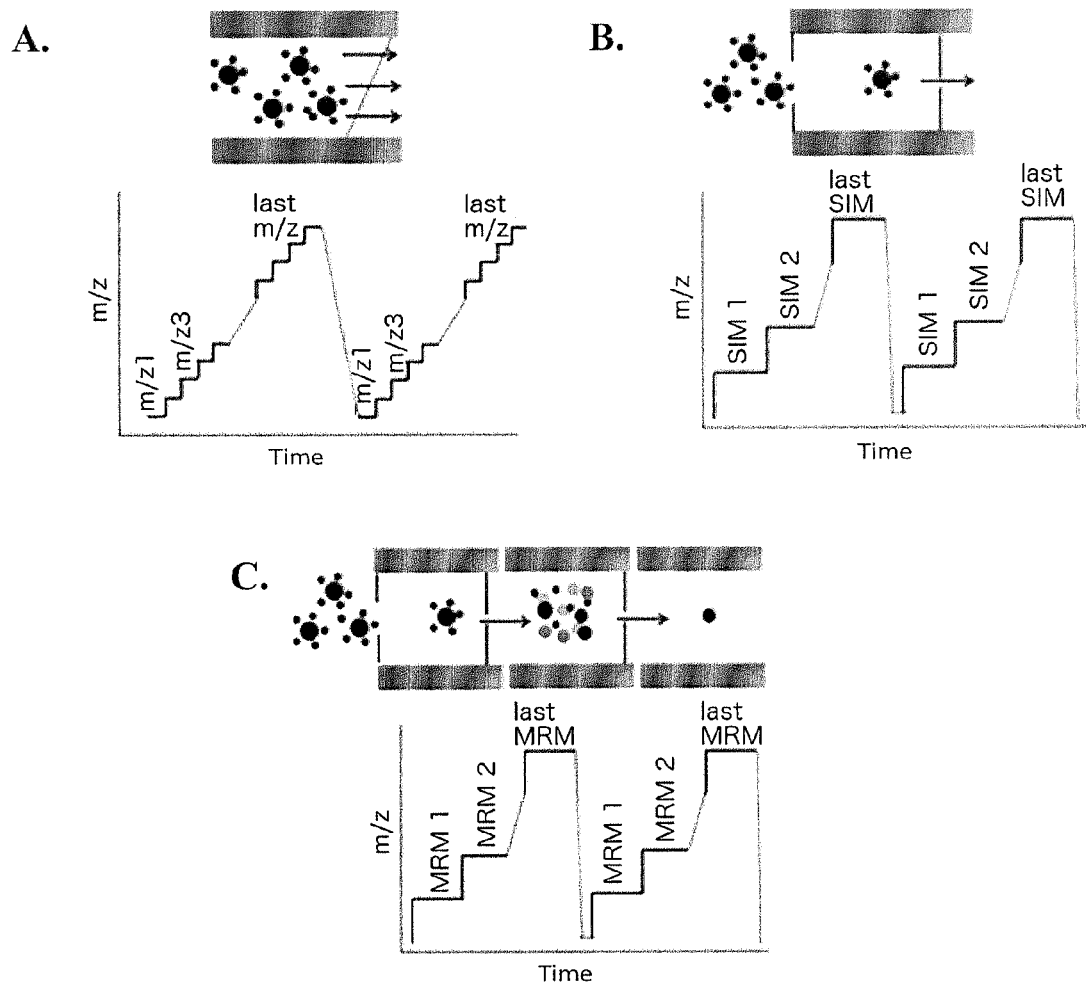
FIG. 1 is a schematic representation of mass spectrometry analysis with different single and triple quadrupole scanning modes: A) a full scan with MS, B) Selected Ion Mode (SIM), C) Multiple Reaction Monitoring (MRM).

Methods of identifying target binding molecules by target guided synthesis are provided. The methods include providing two or more fragments capable of reacting to form the target binding molecule and mixing the fragments with the target. The methods can be used to identify target binding molecules that bind targets such as proteins or nucleic acids, including those that bind shallow binding pockets on the surface of such targets. The methods are applied to the Bcl-XL and Mcl-1 proteins from the Bcl-2 family of proteins. Using thio acid and sulfonyl azide fragments capable of reacting through sulfo-click chemistry, new acyl sulfonamides are identified that bind one or both of the Bcl-XL and Mcl-1 proteins. Compositions and pharmaceutical formulations of these target binding molecules are also provided.

Fragment evolution is a powerful approach for the identification and optimization of inhibitory compounds. Fragment evolution has in particular been successfully applied for the development of potent inhibitors against difficult targets considered to be "undruggable". Kinetic target-guided synthesis (TGS) is a fragment evolution process in which a biological target is exposed to reactive fragments, which under the influence assemble into potent and selective ligands. An improved kinetic TGS approach is described herein, which possess increased throughput enabling the screening of approximately 2000 fragment combinations within less than 12 hours. For example, the methods can screen about 100-10,000, 100-5,000, 200-5,000, or about 200-2,000 fragment combinations in less than 24, 1, 16, 14, 12, 10, or 8 hours. In specific embodiments, the acylium ion is demonstrated herein to be a practical way to analyze multi-component sulfo-click incubation samples. Accordingly, some embodiments provide herein a method of identifying a target binding molecule comprising the use of sulfo-click chemistry, liquid chromatography and triple quadrupole mass spectrometry.

I. Definitions

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides.

The terms "reactive coupling group" and "reactive functional group" are used interchangeably herein to refer to any chemical functional group capable of reacting with a second functional group under the given conditions to form a covalent bond. Those skilled in the art will recognize that some functional groups may react under certain conditions but not under others. Accordingly, some functional groups may be reactive coupling groups only certain conditions, e.g. under conditions where the groups react to form a covalent bond. The selection of reactive coupling groups is within the ability of the skilled artisan. Examples of reactive coupling groups can include primary amines (—NH$_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. Examples of reactive coupling groups can include click reactive coupling groups capable of forming covalent bonds through click reactions. Well-known reactions include the hetero-Diels-Alder reaction, the thiol-ene coupling, the Staudinger ligation, native chemical ligation, and the amidation reaction between thio acids or thio esters and sulfonyl azides (referred to as 'sulfo-click'). As used herein, the terms "sulfo-click" and "sulfo-click chemistry" are used to refer to a reaction between thio acids and sulfonyl azides containing molecules, creating a covalent bonds between the two molecules. Examples of sulfo-click chemistry are described in U.S. Patent Application Publication 2011/0130568 and PCT Publication WO 2012/021486. The coupling reaction may include the use of a catalyst, heat, pH buffers, light, or a combination thereof.

The terms "biocompatible" and "biologically compatible", as used interchangeably herein, refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

The term "subject" refers to any individual who is the target of administration. The subject can be a vertebrate, for example, a mammal. Thus, the subject can be a human. The term does not denote a particular age or sex. The term "patient" refers to a subject afflicted with a disease or disorder. The term "patient" includes human and veterinary subjects.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "preventing", as used herein includes preventing a disease, disorder or condition from occurring in an animal which may be predisposed to the disease, disorder and/or condition but has not yet been diagnosed as having it.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

"Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, subjunctivally, by injection, and by infusion.

Topical administration", as used herein, means the non-invasive administration to the skin, orifices, or mucosa. Topical administrations can be administered locally, i.e. they are capable of providing a local effect in the region of application without systemic exposure. Topical formulations can provide systemic effect via adsorption into the blood stream of the individual. Topical administration can include, but is not limited to, cutaneous and transdermal administration, buccal administration, intranasal administration, intravaginal administration, intravesical administration, ophthalmic administration, and rectal administration.

"Enteral administration", as used herein, means administration via absorption through the gastrointestinal tract. Enteral administration can include oral and sublingual administration, gastric administration, or rectal administration.

"Pulmonary administration", as used herein, means administration into the lungs by inhalation or endotracheal administration. As used herein, the term "inhalation" refers to intake of air to the alveoli. The intake of air can occur through the mouth or nose The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, and $C_3$-$C_{30}$ for branched chains), preferably 20 or fewer, more preferably 15 or fewer, most preferably 10 or fewer. Likewise, preferred cycloalkyls have 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

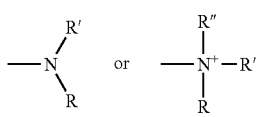

wherein R, R', and R'' each independently represent a hydrogen, an alkyl, an alkenyl, —(CH2)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In preferred embodiments, only one of R or R' can be a carbonyl, e.g., R, R' and the nitrogen together do not form an imide. In still more preferred embodiments, the term "amine" does not encompass amides, e.g., wherein one of R and R' represents a carbonyl. In even more preferred embodiments, R and R' (and optionally R'') each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

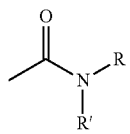

wherein R and R' are as defined above.

"Aryl", as used herein, refers to C$_5$-C$_{10}$-membered aromatic, heterocyclic, fused aromatic, fused heterocyclic, biaromatic, or biheterocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl".

The term "aralkyl", as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle", as used herein, refers to an aromatic or non-aromatic ring(s) in which each atom of the ring(s) is carbon.

"Heterocycle" or "heterocyclic", as used herein, refers to a monocyclic or bicyclic structure containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, (C$_1$-C$_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbonyl" is art-recognized and includes such moieties as can be represented by the general formula:

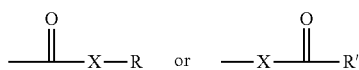

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid". Where X is an oxygen and R' is hydrogen, the formula represents a "formate". In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur, and selenium. Other heteroatoms include silicon and arsenic.

As used herein, the term "nitro" means —NO$_2$; the term "halogen" designates —F, —Cl, —Br, or —I; the term "sulfhydryl" means —SH; the term "hydroxyl" means —OH; and the term "sulfonyl" means —SO$_2$ The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

II. Methods of Identifying Target-Binding Molecules

Methods of identifying target binding molecules are provided herein. The methods are capable of rapidly screening many possible target binding molecules. For example, the methods can in some embodiments screen more than about 100, 500, 1,000, or even 2,000 potential target binding molecules in less than about 24, 18, 12, 10, or even 8 hours. The target binding molecules can be formed by the target-guided synthesis starting from two or more fragments having complimentary reactive coupling groups. More specifically, in some embodiments, provided herein is a method of identifying a target binding molecule comprising
 a) providing a plurality of first fragments having a first reactive coupling group;
 b) providing a plurality of second fragments comprising a second reactive coupling group capable of forming a covalent bond with the first reactive coupling group of the first fragments;
 c) combining the first fragments and the second fragments in a mixture with the target;
 d) reacting at least one of the first fragments with at least one of the second fragments to form one or more target binding molecules; and
 e) analyzing the mixture with a tandem mass spectrometer to identify a fragmentation product and identify the target binding molecule(s) corresponding to the fragmentation product.

A. Fragments

Fragments are provided herein that are capable of reacting to form a target binding molecule in the presence of a target. The fragments can include a first plurality of fragments and a second plurality of fragments capable of reacting with fragments from the first plurality to form a target binding molecule. The first plurality of fragments can include a plurality of different fragments each having a first reactive coupling group. The second plurality of fragments can include a plurality of different fragments each having a second reactive coupling group capable of forming a covalent bond with the first reactive coupling group of the first plurality of fragments.

The fragments from the first plurality of fragments and the second plurality of fragments can include "click-able" fragments, i.e. fragments capable of reacting via click chemistry to form a covalent bond between the fragments. For example, the fragments can include thio acids and sulfonyl azides. In some embodiments, the first reactive coupling group is a thio acid moiety and the second reactive coupling group is a sulfonyl azide moiety. It may be advantageous in certain embodiments to provide the plurality of fragments comprising a sulfonyl azide moiety in a larger amount than the plurality of fragments comprising a thio acid or thio ester moiety. In some embodiments, the sulfonyl azide containing fragments are 2 times, 5 times, 10 times, or 20 times greater in amount than the thio acid or thio ester containing fragments. In some embodiments, the plurality of first fragments have thio ester moieties that are converted in situ to a thio acid moiety.

The fragments can include any combination of reactive coupling groups capable of forming a covalent bond under the conditions of the method. For example, the fragments can be incubated in a mixture with the target for a period of time of about 1-24, 1-18, 1-14, 2-14, 4-14, or 6-12 hours.

The fragments can be incubated in a mixture with the target in the presence of a buffer. The fragments can be incubated in a mixture with the target at a pH of about 6-8, 6.5-8, 6.5-7.5, or 7-7.5. The fragments can be incubated with the target at a temperature of about 30-50° C., 30-45° C., 32-45° C., 32-40° C., or 35-40° C.

In some embodiments the fragments include one or more thioesters selected from TE1, TE2, TE3, TE5, TE7, TE8, TE14, TE15, TE17, TE20, TE21, TE23, TE24, TE25, TE30, TE31, TE34, TE40, TE41, TE42, TE44, or TE45 having the structures shown below.

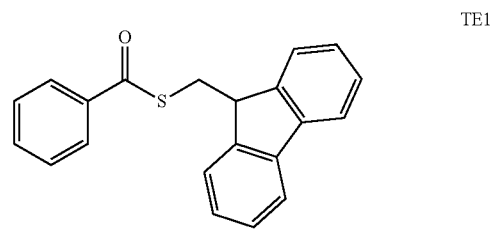

TE1

$C_{21}H_{16}OS$

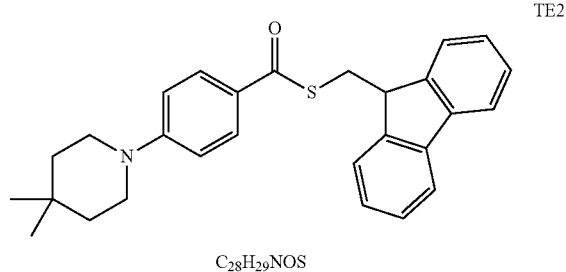

TE2

$C_{28}H_{29}NOS$

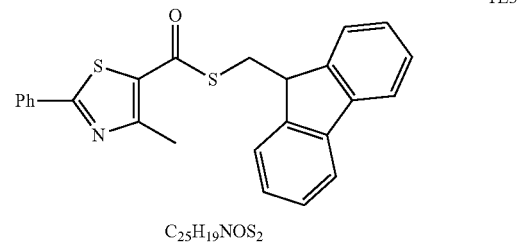

TE3

$C_{25}H_{19}NOS_2$

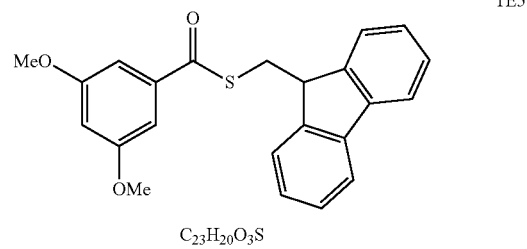

TE5

$C_{23}H_{20}O_3S$

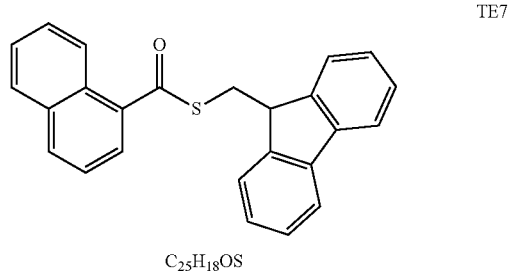

TE7

$C_{25}H_{18}OS$

-continued
TE8
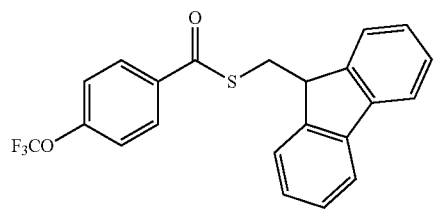
C₂₂H₁₅F₃O₂S
TE14
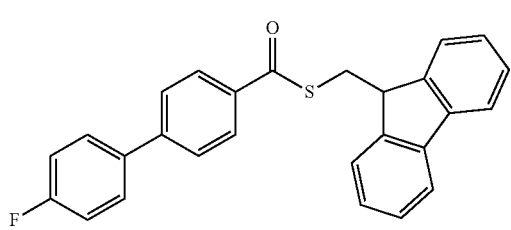
C₂₇H₁₉FOS
TE15
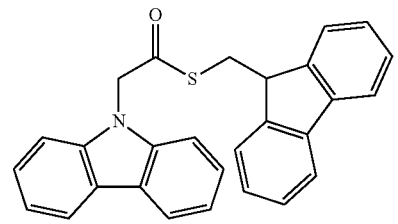
C₂₈H₂₁NOS
TE17
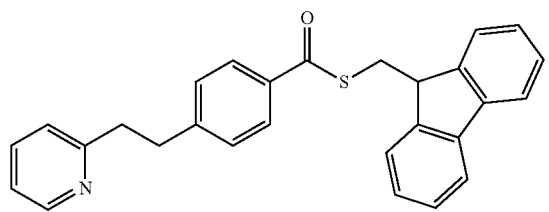
C₂₈H₂₃NOS
TE20
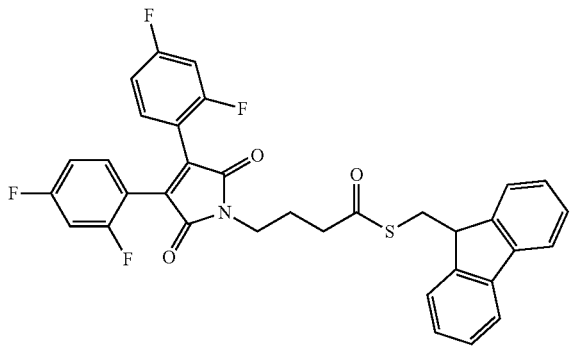
C₃₄H₂₃F₄NO₃S
-continued
TE21
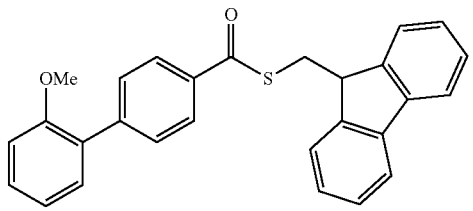
C₂₈H₂₂O₂S
TE23
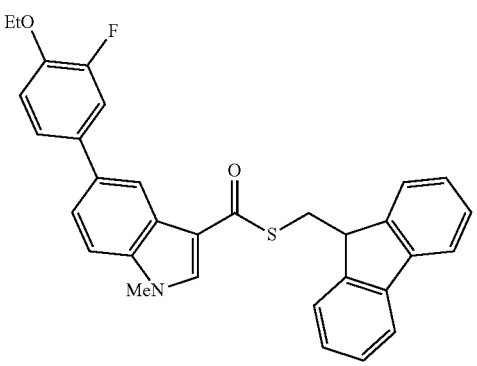
C₃₂H₂₆FNO₂S
TE24
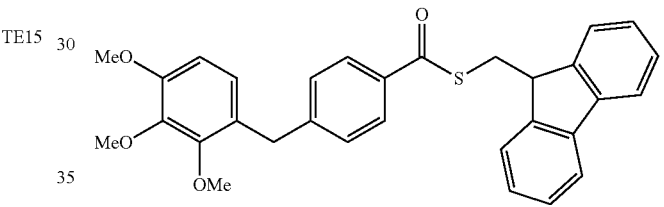
C₃₁H₂₈O₄S
TE25
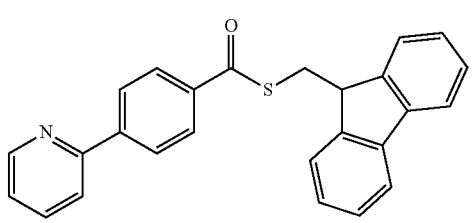
C₂₆H₁₉NOS
TE30
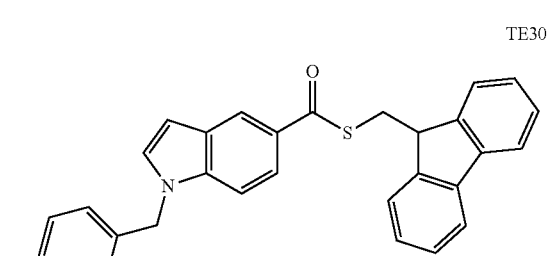
C₃₂H₂₁F₆NOS -continued

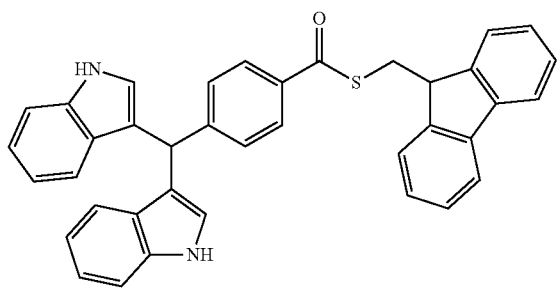

TE31

C$_{38}$H$_{28}$N$_2$OS

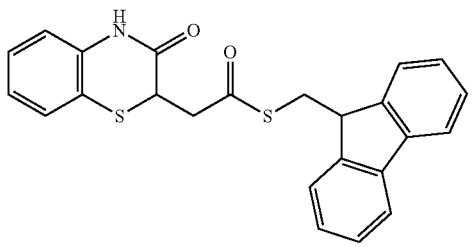

TE34

C$_{24}$H$_{19}$NO$_2$S$_2$

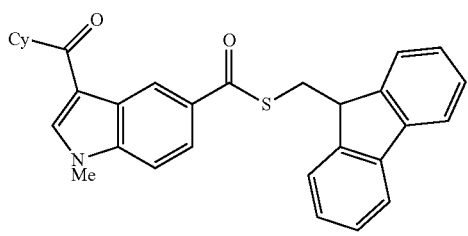

TE40

C$_{31}$H$_{29}$NO$_2$S$_2$

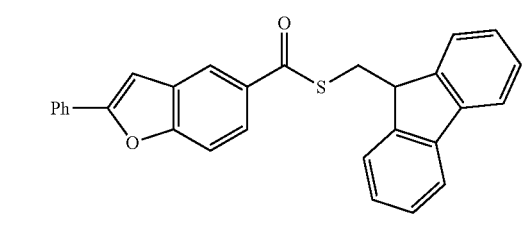

TE41

C$_{29}$H$_{20}$O$_2$S

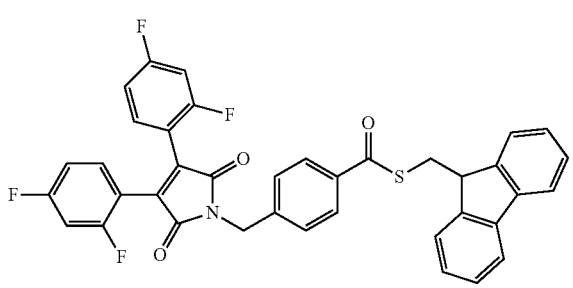

TE42

C$_{38}$H$_{23}$F$_4$NO$_3$S

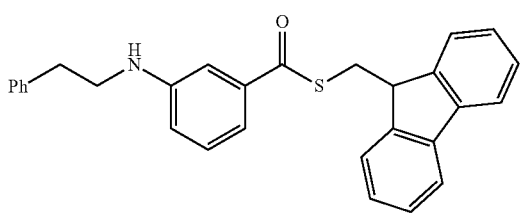

TE44

C$_{29}$H$_{25}$NOS

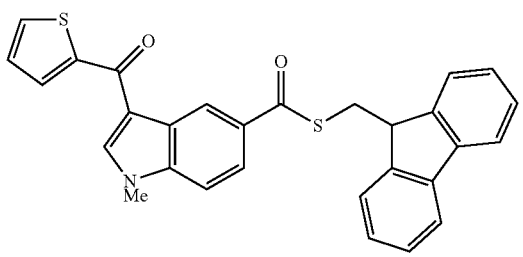

TE45

C$_{29}$H$_{21}$NO$_2$S$_2$

In some embodiments the fragments include one or more sulfonyl azides selected from SZ1, SZ2, SZ4, SZ6, SZ7, SZ8, SZ9, SZ10, SZ11, SZ12, SZ14, SZ15, SZ16, SZ17, SZ21, SZ23, SZ24, SZ27, SZ28, SZ31, SZ32, SZ34, SZ35, SZ36, or SZ37 having the structures shown below.

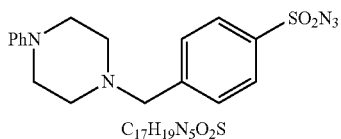

SZ1

C$_{17}$H$_{19}$N$_5$O$_2$S

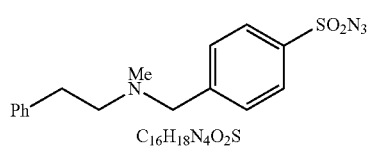

SZ2

C$_{16}$H$_{18}$N$_4$O$_2$S

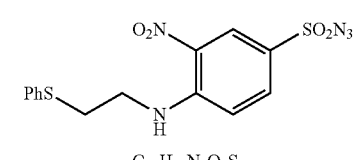

SZ4

C$_{14}$H$_{13}$N$_5$O$_4$S$_2$

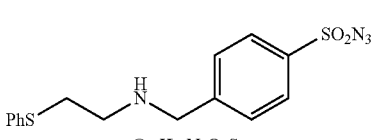

SZ6

C$_{15}$H$_{16}$N$_4$O$_2$S$_2$

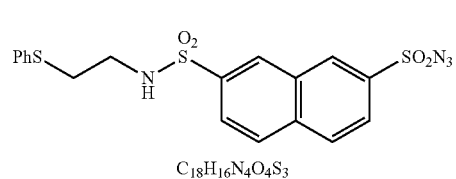

SZ7

C$_{18}$H$_{16}$N$_4$O$_4$S$_3$

-continued
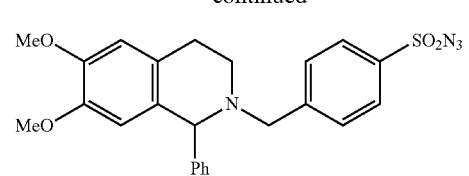
SZ8
C₂₄H₂₄N₄O₄S
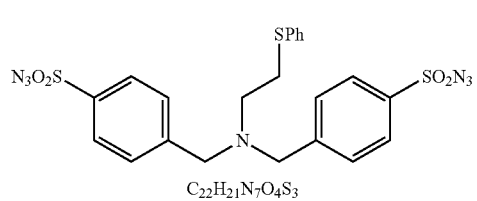
SZ9
C₂₂H₂₁N₇O₄S₃
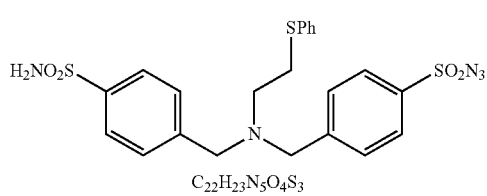
SZ10
C₂₂H₂₃N₅O₄S₃
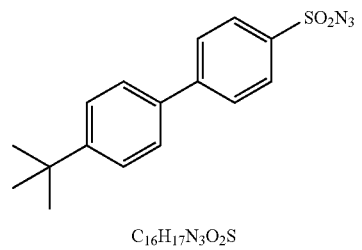
SZ11
C₁₆H₁₇N₃O₂S
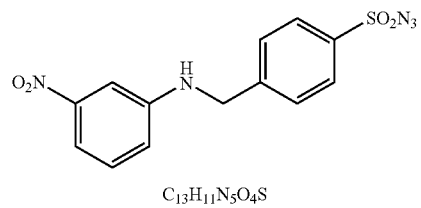
SZ12
C₁₃H₁₁N₅O₄S
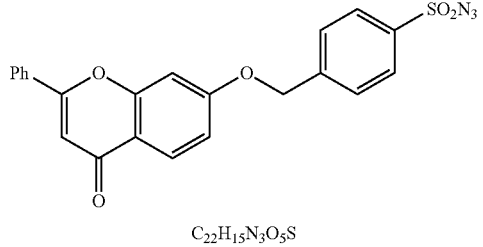
SZ14
C₂₂H₁₅N₃O₅S
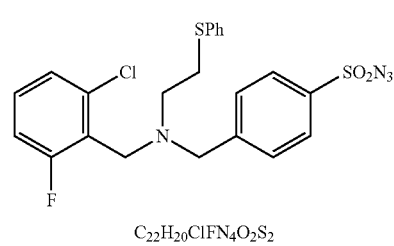
SZ15
C₂₂H₂₀ClFN₄O₂S₂
-continued
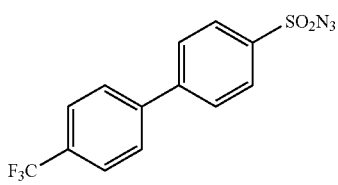
SZ16
C₁₃H₈F₃N₃O₂S
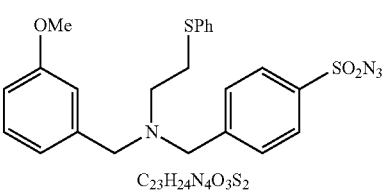
SZ17
C₂₃H₂₄N₄O₃S₂
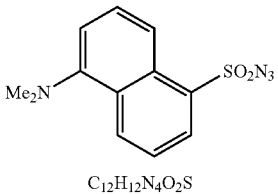
SZ21
C₁₂H₁₂N₄O₂S
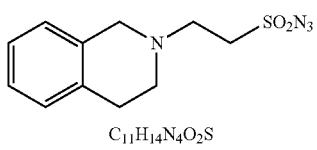
SZ23
C₁₁H₁₄N₄O₂S
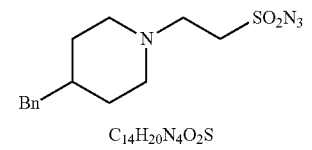
SZ24
C₁₄H₂₀N₄O₂S
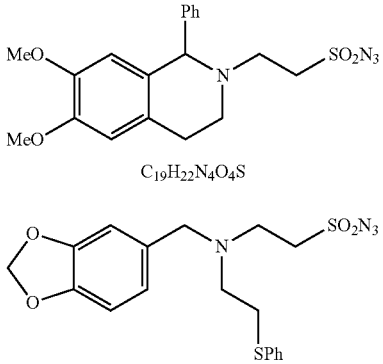
SZ27
C₁₉H₂₂N₄O₄S
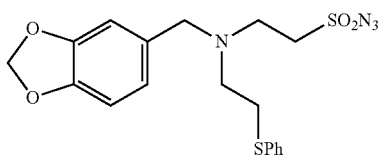
SZ28
C₁₈H₂₀N₄O₄S₂
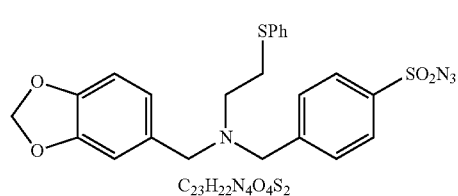
SZ31
C₂₃H₂₂N₄O₄S₂

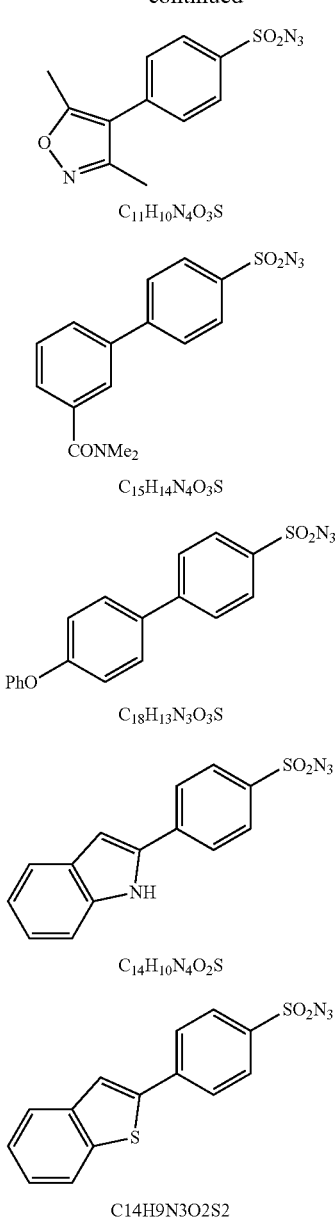

SZ32 C${}_{11}$H${}_{10}$N${}_{4}$O${}_{3}$S

SZ34 C${}_{15}$H${}_{14}$N${}_{4}$O${}_{3}$S

SZ35 C${}_{18}$H${}_{13}$N${}_{3}$O${}_{3}$S

SZ36 C${}_{14}$H${}_{10}$N${}_{4}$O${}_{2}$S

SZ37 C14H9N3O2S2

B. Targets

The term "target" refers herein to any molecule that can be bound by a target binding molecule described herein. The target can be a polypeptide or a polynucleotide (including deoxyribonucleotides and ribonucleotides). The target can be one of a polypeptide-polypeptide, polypeptide-DNA, or polypeptide-RNA binding pair.

The target can be a protein of the Bcl-2 family. The proteins of the anti-apoptotic Bcl-2 family, namely Bcl-2, Bcl-Xl, and Mcl-1 are among the protein-protein interaction targets that have been validated for cancer therapy. Bcl proteins are central regulators of programmed cell death. They are overexpressed in many cancers and contribute to tumor initiation, progression, and resistance to therapy. The conserved BH3 domain within the pro-apoptotic Bcl-2 family has been shown to be critical for their cell death-inducing function. Several efforts to develop low molecular weight compounds that mimic the BH3 domain of pro-apoptotic Bcl proteins have been reported in recent years. While a small number of compounds with potent anti-Bcl-2 and anti-Bcl-X${}_L$ activity have been discovered, only a few compounds are known to interact with Mcl-7. However, accumulating evidence suggests that it is advantageous to develop compounds selectively targeting Mcl-2, Bcl-2 or Bcl-X${}_L$ to induce apoptosis in most types of cancer. Accordingly, in some embodiments, the target is Bcl-X${}_L$. In other embodiments, the target is Mcl-1.

C. Tandem Mass Spectrometry

The term "tandem mass spectrometer" is used herein to refer to instruments capable of multiple step mass spectrometry selection with some fragmentation occurring between the stages. The stages of mass analysis separation can be from individual mass spectrometer elements separated in space or from a single mass spectrometer with the mass spectrometry steps separated in time. Tandem mass spectrometers can include, among others, QqTOF mass spectrometers, triple quadrupole mass spectrometers, ion trap mass spectrometers, ion trap time-of-flight (TOF) mass spectrometers, ion cyclotron resonance (ICR) mass spectrometers, time-of-flight time-of-flight (TOF-TOF) mass spectrometers, Fourier transform ion cyclotron resonance mass spectrometers, electric sector-magnetic sector mass spectrometers, magnetic sector-electric sector mass spectrometers, and electric sector-electric sector mass spectrometers.

Tandem mass spectrometers can be used to identify a fragmentation product and one or more target binding molecules that produced the fragmentation produce. This allows the tandem mass spectrometer to screen many potential target binding molecules in a short period of time. In some embodiments the tandem mass spectrometer is operated in multiple reaction monitoring (MRM) mode.

Triple quadrupole mass spectrometry is a tandem mass spectrometer having two quadrupole mass spectrometers in series, with a radio frequency-only quadrupole between them. The first (Q1) and third (Q3) quadrupoles serve as mass filters. Precursor ions selected in Q1 are dissociated in a collision cell in the presence of an inert gas such as Ar, He or N${}_2$. Resulting fragments are passed through to Q3 where they may be filtered or scanned. Triple quadrupole mass spectrometry can be performed in several different modes: product ion scan, precursor ion scan, neutral loss scan, selected reaction monitoring, and multiple reaction monitoring. In selected reaction monitoring, Q1 and Q3 are set to a selected mass. In multiple reaction monitoring, Q1 and/or Q3 are set to more than a single mass. In one embodiment, triple quadrupole mass spectrometry is performed in a multiple reaction monitoring mode. In some further embodiments, Q3 is set to a mass of an acylium ion.

D. Target Binding Molecules

Target binding molecules are provided herein. Target binding molecules can be identified using the methods described above and exemplified in the examples below. The target binding molecules can be formed by the covalent bonding of a fragment from the first plurality of fragments described above and a fragment from the second plurality of fragments described above. In some embodiments the target binding molecule is an acyl sulfonamide. In some embodiments the target binding molecule is an acyl sulfonamide identified in FIGS. 5A-5N or in Table 3. In some embodiments the target binding molecule is an acyl sulfonamide formed by reacting a thio ester identified in FIGS. 4D-4H with a sulfonyl azide identified in FIGS. 4A-4C.

The methods can be used to identify target binding molecules that can bind the target with high affinity. For example, the target binding molecules can have an $IC_{50}$ for the target of less than about 100 μM, e.g. less than about 90, 80, 70, 60, 50 25, 10, or 5 μM.

In some embodiments the target binding molecule is an acyl sulfonamide selected from SZ10TA15, SZ10TA2, SZ10TA20, SZ10TA21, SZ10TA25, SZ10TA34, SZ10TA40, SZ10TA41, SZ10TA44, SZ11TA25, SZ11TA30, SZ11TA40, SZ12TA2, SZ12TA23, SZ12TA42, SZ14TA40, SZ14TA42, SZ15TA1, SZ15TA14, SZ15TA15, SZ15TA17, SZ15TA24, SZ15TA25, SZ15TA3, SZ15TA34, SZ15TA5, SZ15TA7, SZ15TA8, SZ16TA21, SZ16TA44, SZ17TA14, SZ17TA15, SZ17TA17, SZ17TA20, SZ17TA24, SZ17TA25, SZ17TA3, SZ17TA30, SZ17TA40, SZ17TA45, SZ17TA7, SZ17TA8, SZ1TA14, SZ1TA23, SZ1TA30, SZ21TA23, SZ23TA2, SZ24TA30, SZ27TA42, SZ28TA30, SZ28TA31, SZ28TA45, SZ2TA31, SZ31TA14, SZ31TA15, SZ31TA17, SZ31TA24, SZ31TA3, SZ31TA30, SZ31TA31, SZ31TA40, SZ31TA44, SZ31TA45, SZ31TA8, SZ32TA42, SZ34TA42, SZ35TA17, SZ35TA24, SZ35TA3, SZ35TA7, SZ36TA2, SZ37TA42, SZ4TA17, SZ4TA21, SZ4TA30, SZ6TA23, SZ7TA2, SZ7TA23, SZ7TA45, SZ8TA14, SZ8TA2, SZ8TA20, SZ8TA24, SZ8TA31, SZ9TA1, SZ9TA14, SZ9TA17, SZ9TA20, SZ9TA25, SZ9TA3, SZ9TA5, or SZ9TA7, the structures of which are shown below.

SZ10TA15

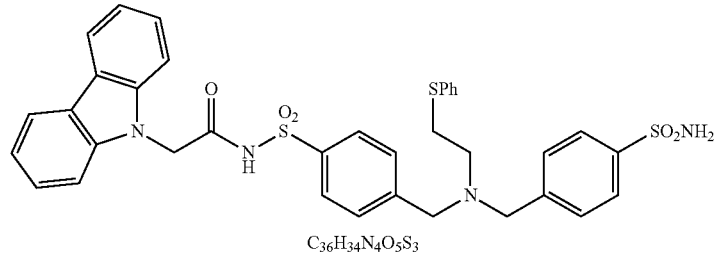

SZ10TA2

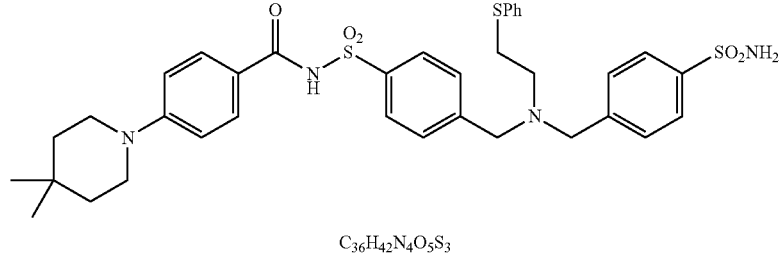

SZ10TA20

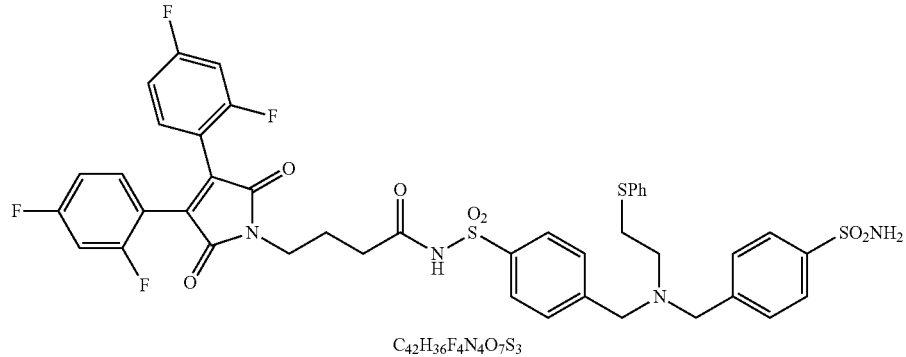

SA10TA21

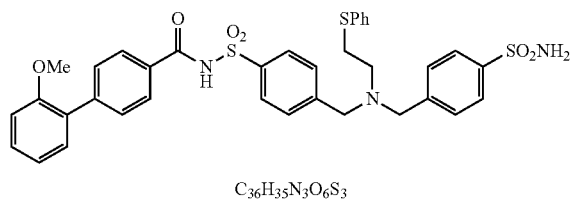

SZ10TA25

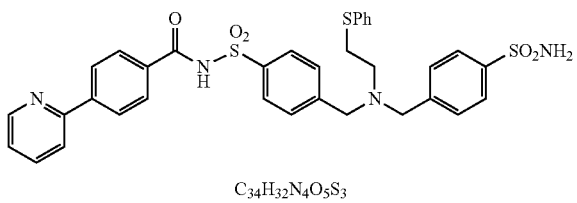

SZ10TA34
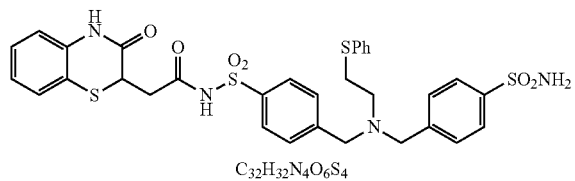
C$_{32}$H$_{32}$N$_4$O$_6$S$_4$
SZ10TA40
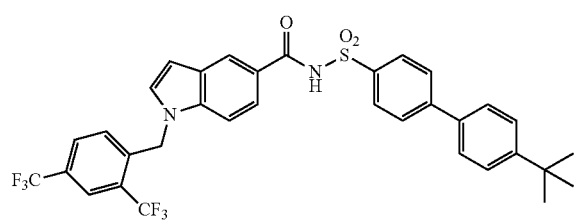
C$_{39}$H$_{42}$N$_4$O$_6$S$_3$
SZ10TA41
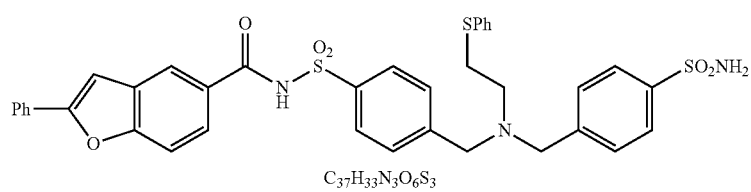
C$_{37}$H$_{33}$N$_3$O$_6$S$_3$
SZ10TA44
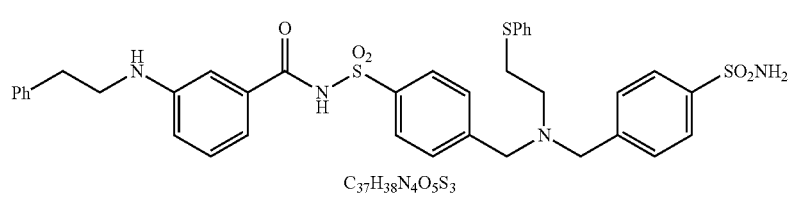
C$_{37}$H$_{38}$N$_4$O$_5$S$_3$
SZ11TA25
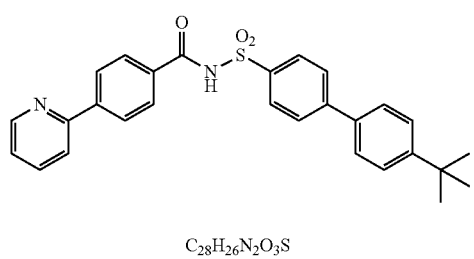
C$_{28}$H$_{26}$N$_2$O$_3$S
SZ11TA30
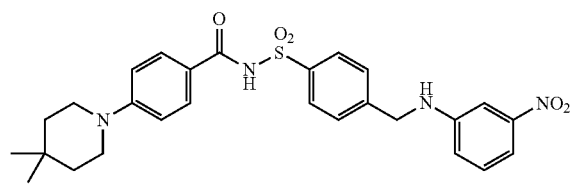
C$_{34}$H$_{28}$F$_6$N$_2$O$_3$S
SZ11TA40
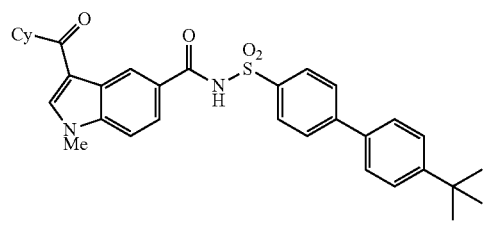
C$_{33}$H$_{36}$N$_2$O$_4$S
SZ12TA2
C$_{27}$H$_{30}$N$_4$O$_5$S
SZ12TA23
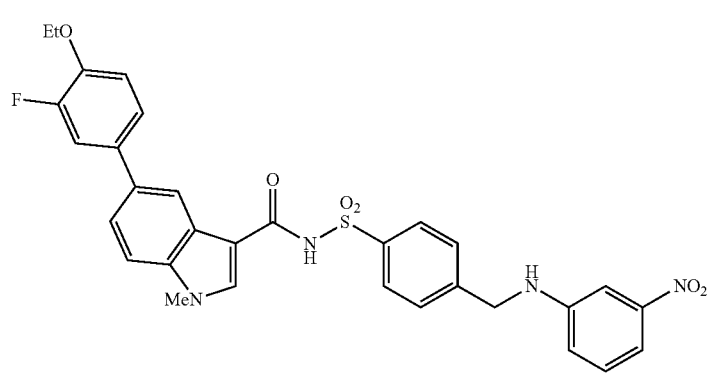
C$_{31}$H$_{27}$FN$_4$O$_6$S -continued
SZ12TA42
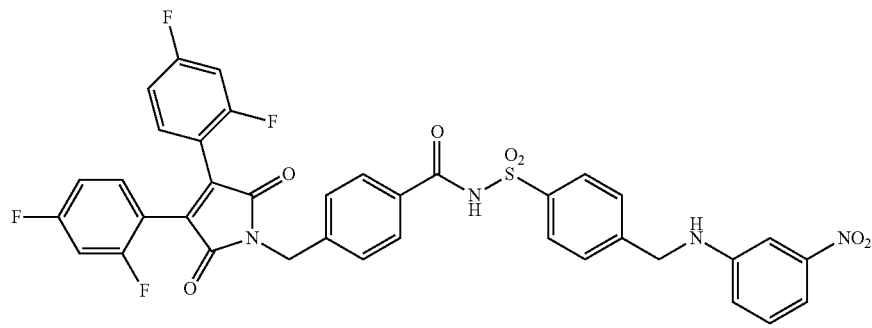
C₃₇H₂₄F₄N₄O₇S
SZ14TA40
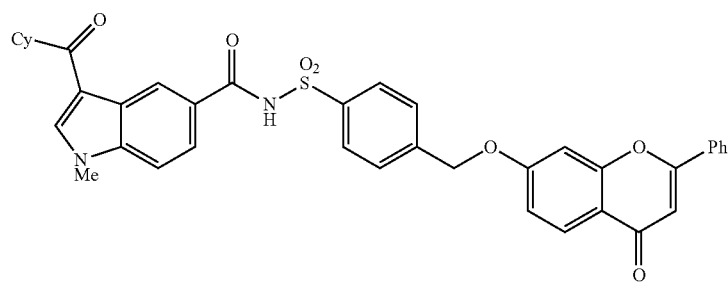
C₃₉H₃₄N₂O₇S
SZ14TA42
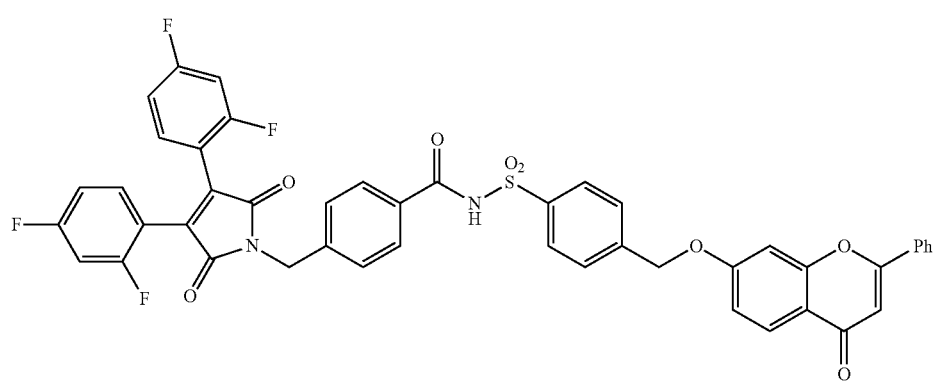
C₄₆H₂₈F₄N₂O₈S
SZ15TA1
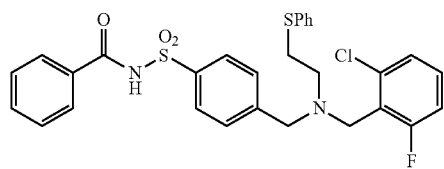
C₂₉H₂₆ClFN₂O₃S₂
SZ15TA14
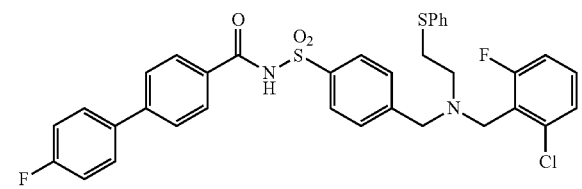
C₃₅H₂₉ClF₂N₂O₃S₂
SZ15TA15
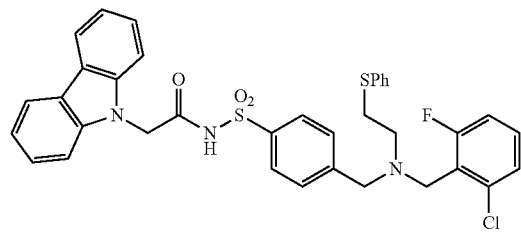
C₃₆H₃₁ClFN₃O₃S₂
SZ15TA17
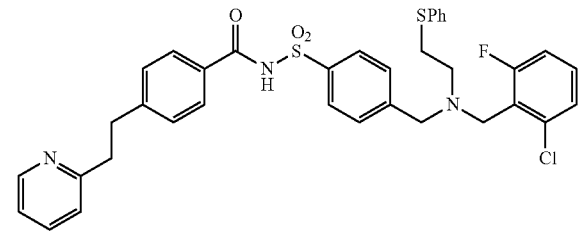
C₃₆H₃₃ClFN₃O₃S₂

SZ15TA24
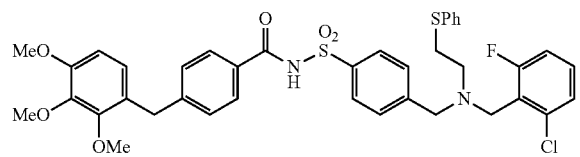
C₃₉H₃₈ClFN₂O₆S₂
SZ15TA25
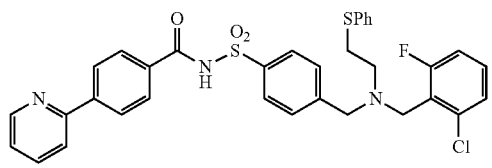
C₃₄H₂₉ClFN₃O₃S₂
SZ15TA3
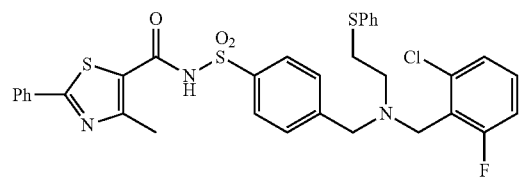
C₃₃H₂₉ClFN₃O₃S₃
SZ15TA34
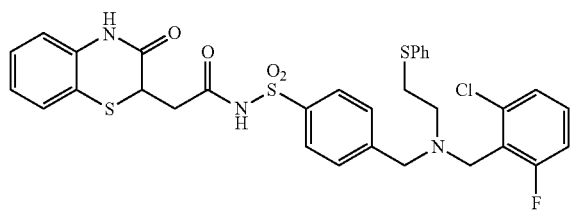
C₃₂H₂₉ClFN₃O₄S₃
SZ15TA7
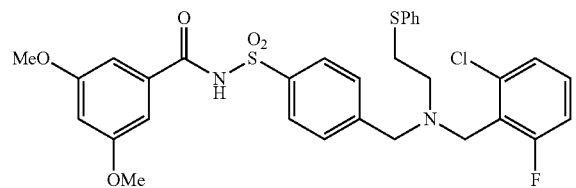
C₃₁H₃₀ClFN₂O₅S₂
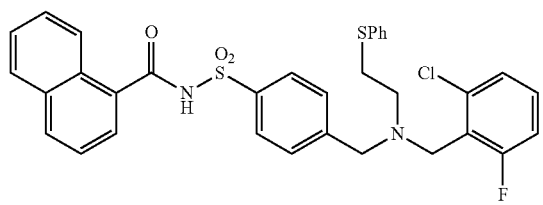
C₃₃H₂₈ClFN₂O₃S₂
SZ16TA8
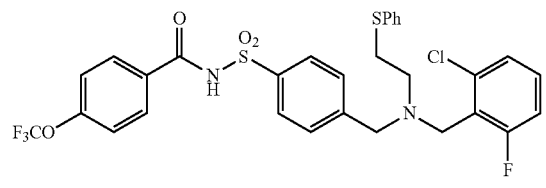
C₃₀H₂₅ClF₄N₂O₄S₂
SZ16TA21
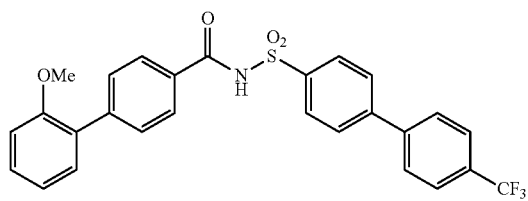
C₂₇H₂₀F₃NO₄S
SZ16TA44
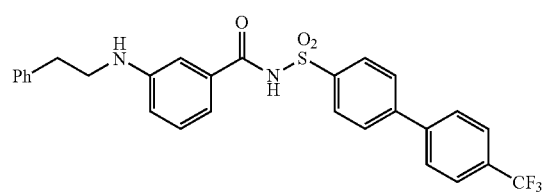
C₂₈H₂₃F₃N₂O₃S
SZ17TA14
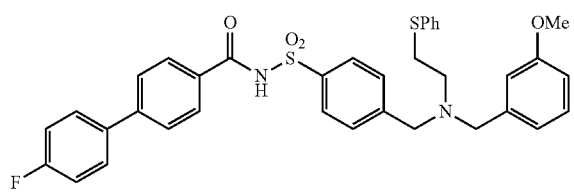
C₃₆H₃₃FN₂O₄S₂
SZ17TA15
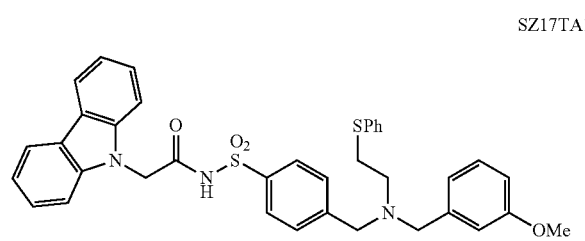
C₃₇H₃₅N₃O₄S₂
SZ17TA17
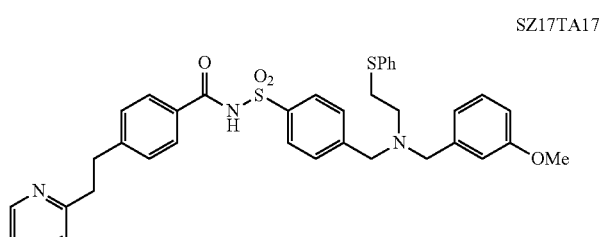
C₃₇H₃₇N₃O₄S₂

-continued
SZ17TA20
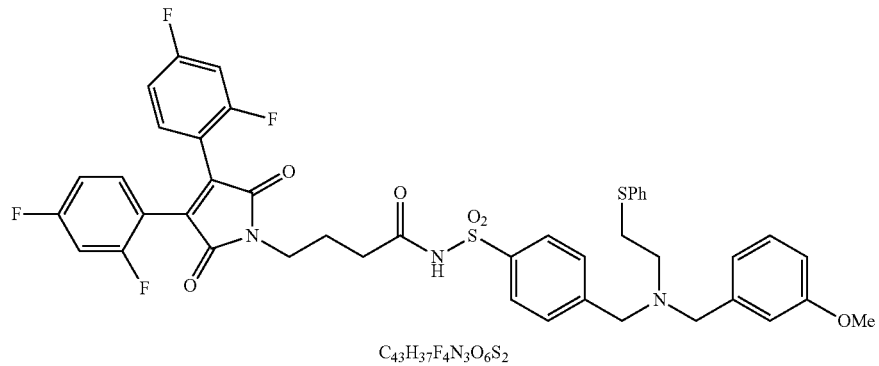
C$_{43}$H$_{37}$F$_4$N$_3$O$_6$S$_2$
SZ17TA24
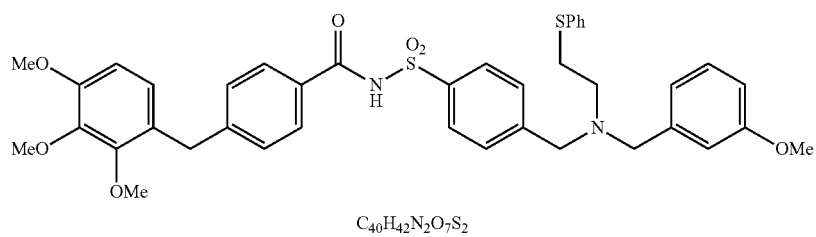
C$_{40}$H$_{42}$N$_2$O$_7$S$_2$
SZ17TA25
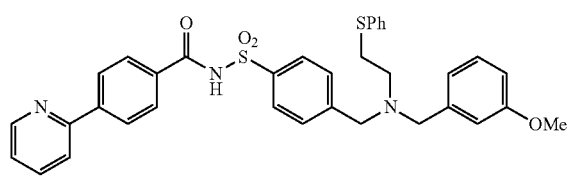
C$_{35}$H$_{33}$N$_3$O$_4$S$_2$
SZ17TA3
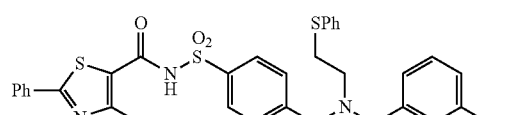
C$_{34}$H$_{33}$N$_3$O$_4$S$_3$
SZ17TA30
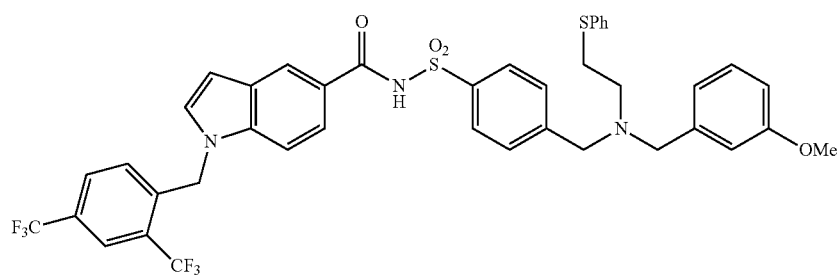
C$_{41}$H$_{35}$F$_6$N$_3$O$_4$S$_2$
SZ17TA40
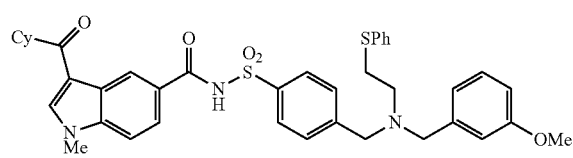
C$_{40}$H$_{43}$N$_3$O$_5$S$_2$
SZ17TA45
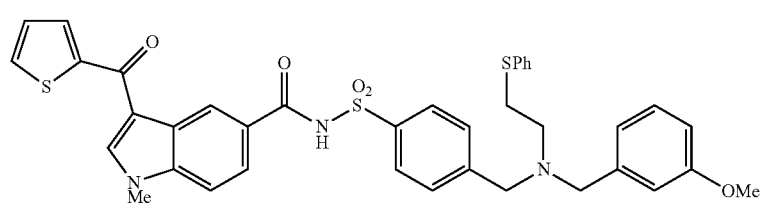
C$_{38}$H$_{35}$N$_3$O$_5$S$_3$ -continued
SZ17TA7
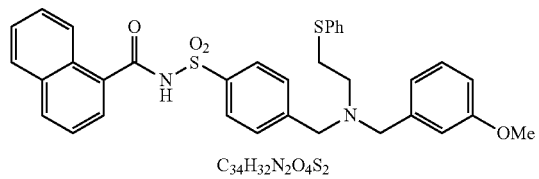
C₃₄H₃₂N₂O₄S₂
SZ17TA8
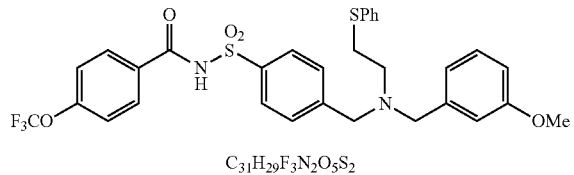
C₃₁H₂₉F₃N₂O₅S₂
SZ1TA14
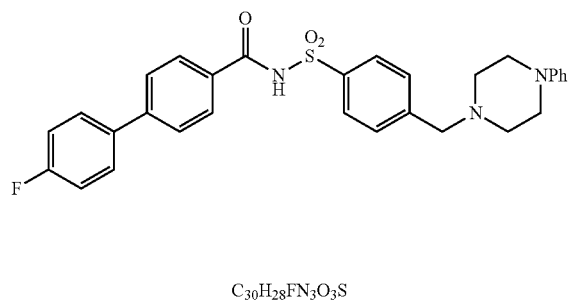
C₃₀H₂₈FN₃O₃S
SZ1TA23
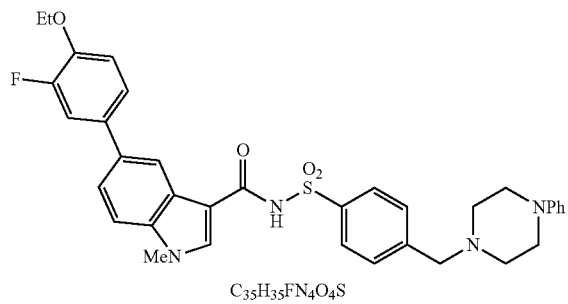
C₃₅H₃₅FN₄O₄S
SZ1TA30
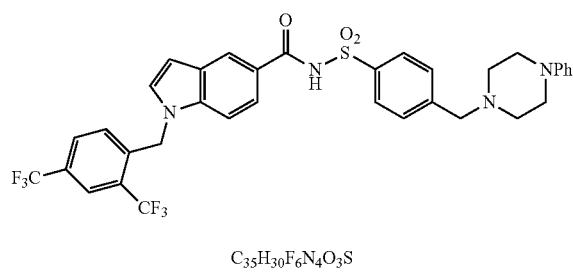
C₃₅H₃₀F₆N₄O₃S
SZ21TA23
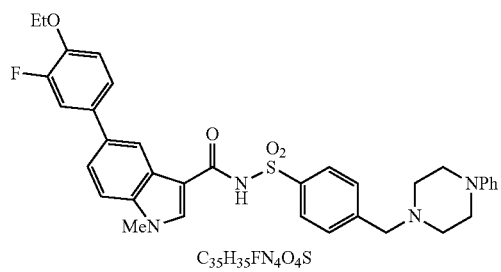
C₃₅H₃₅FN₄O₄S
SZ23TA2
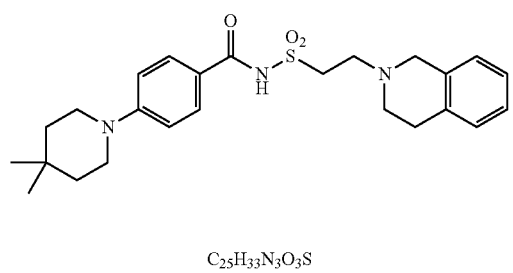
C₂₅H₃₃N₃O₃S
SZ24TA30
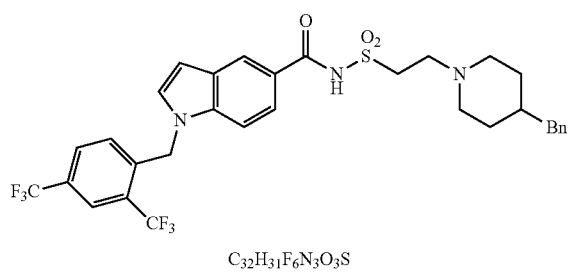
C₃₂H₃₁F₆N₃O₃S
SZ27TA42
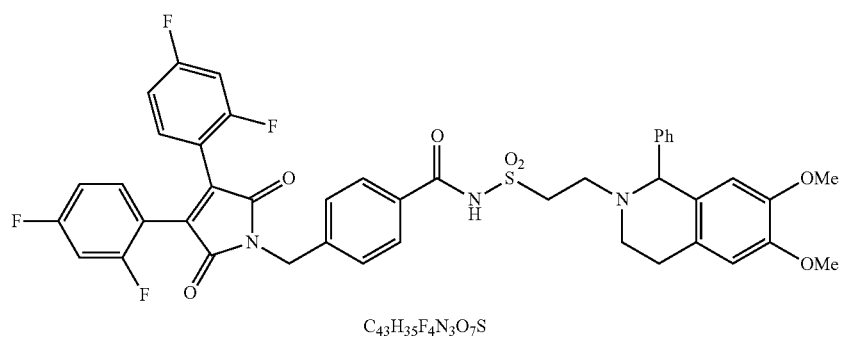
C₄₃H₃₅F₄N₃O₇S -continued
SZ28TA30
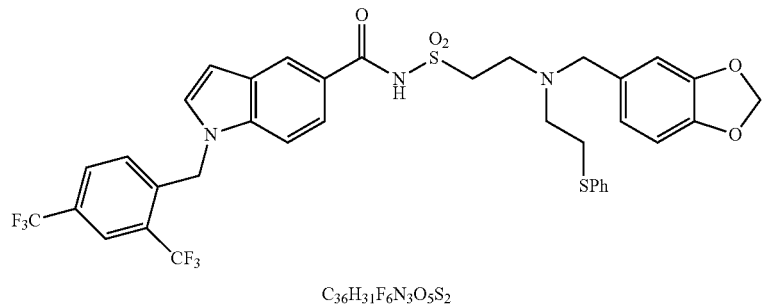
C$_{36}$H$_{31}$F$_6$N$_3$O$_5$S$_2$
SZ28TA31
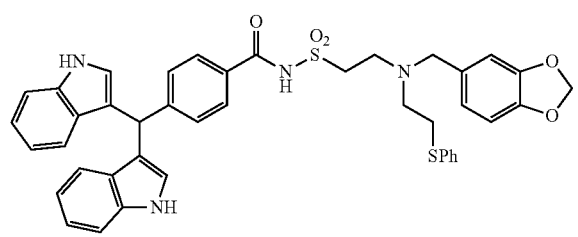
SZ28TA45
C$_{33}$H$_{31}$N$_3$O$_6$S$_3$
SZ2TA31
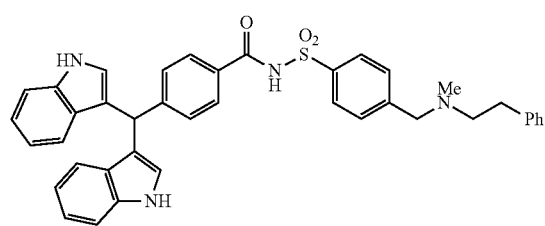
C$_{40}$H$_{36}$N$_4$O$_3$S
SZ31TA14
C$_{36}$H$_{31}$FN$_2$O$_5$S$_2$
SZ31TA15
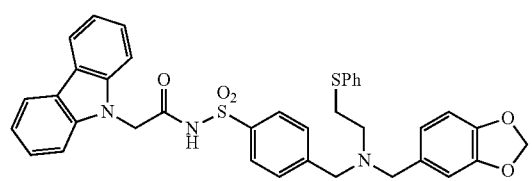
SZ31TA17
C$_{37}$H$_{33}$N$_3$O$_5$S$_2$
C$_{37}$H$_{35}$N$_3$O$_5$S$_2$
SZ31TA24
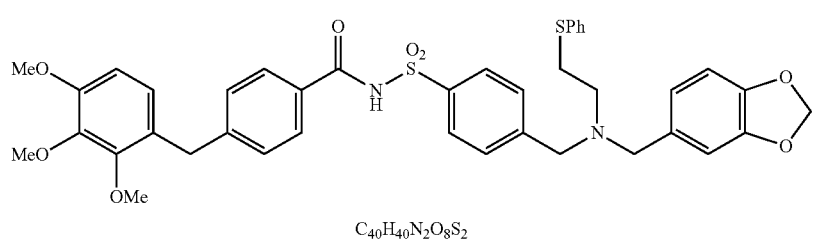
C$_{40}$H$_{40}$N$_2$O$_8$S$_2$
SZ31TA3
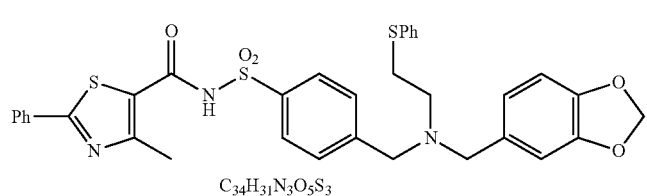
C$_{34}$H$_{31}$N$_3$O$_5$S$_3$

SZ31TA30

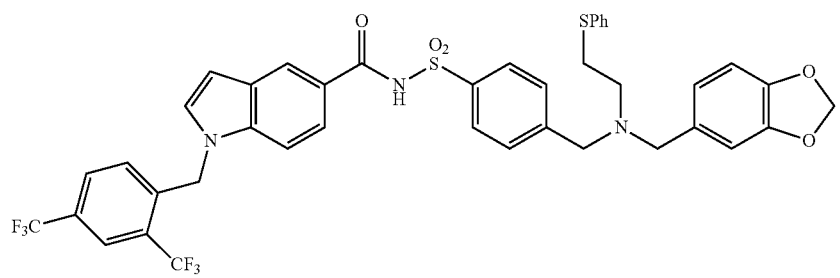

C<sub>41</sub>H<sub>33</sub>F<sub>6</sub>N<sub>3</sub>O<sub>5</sub>S<sub>2</sub>

SZ31TA31

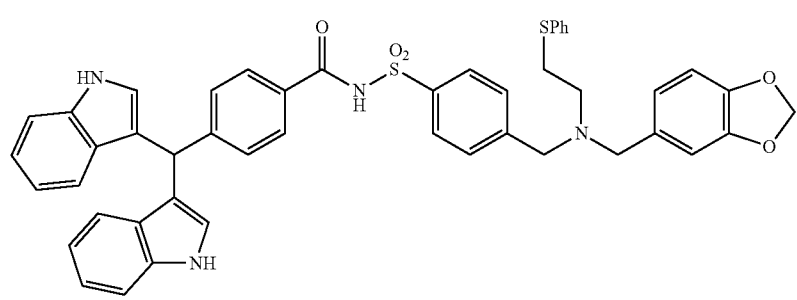

C<sub>47</sub>H<sub>40</sub>N<sub>4</sub>O<sub>5</sub>S<sub>2</sub>

SZ31TA40

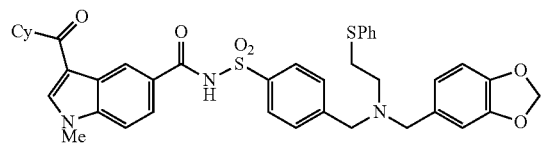

C<sub>40</sub>H<sub>41</sub>N<sub>3</sub>O<sub>6</sub>S<sub>2</sub>

SZ31TA44

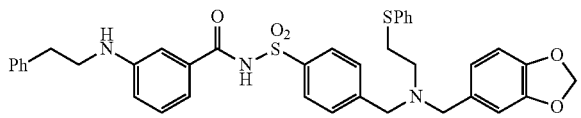

C<sub>38</sub>H<sub>37</sub>N<sub>3</sub>O<sub>5</sub>S<sub>2</sub>

SZ31TA45

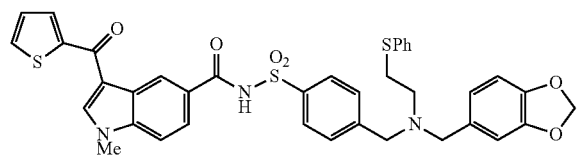

C<sub>38</sub>H<sub>33</sub>N<sub>3</sub>O<sub>6</sub>S<sub>3</sub>

SZ31TA8

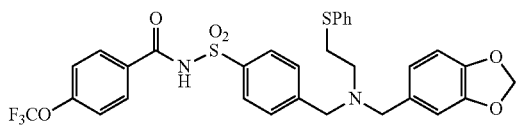

C<sub>31</sub>H<sub>27</sub>F<sub>3</sub>N<sub>2</sub>O<sub>6</sub>S<sub>2</sub>

SZ32TA42

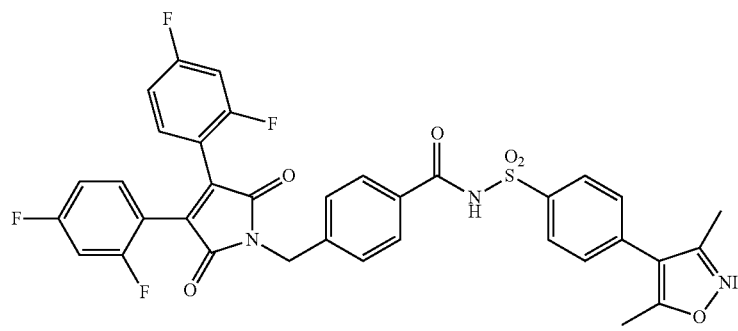

C<sub>35</sub>H<sub>23</sub>F<sub>4</sub>N<sub>3</sub>O<sub>6</sub>S

-continued
SZ34TA42
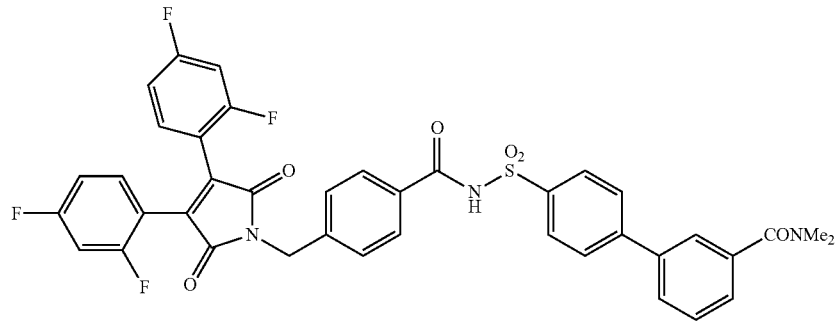
C₃₉H₂₇F₄N₃O₆S
SZ35TA17
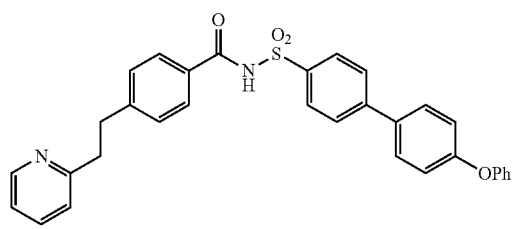
C₃₂H₂₆N₂O₄S
SZ35TA24
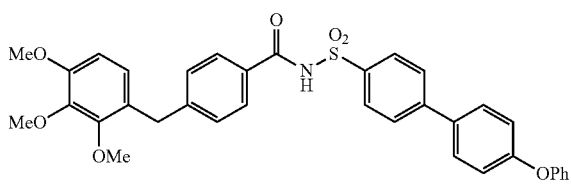
C₃₅H₃₁NO₇S
SZ35TA3
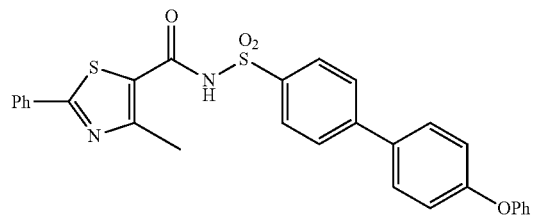
C₂₉H₂₂N₂O₄S₂
SZ35TA7
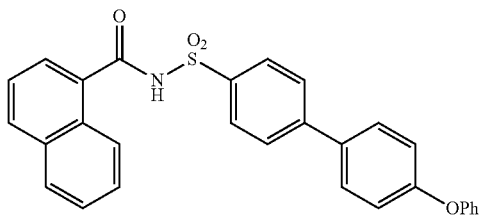
C₂₉H₂₁NO₄S
SZ36TA2
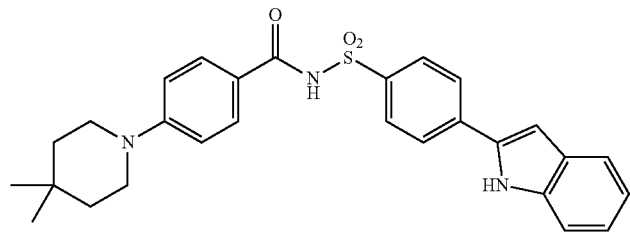
C₂₈H₂₉N₃O₃S
SZ37TA42
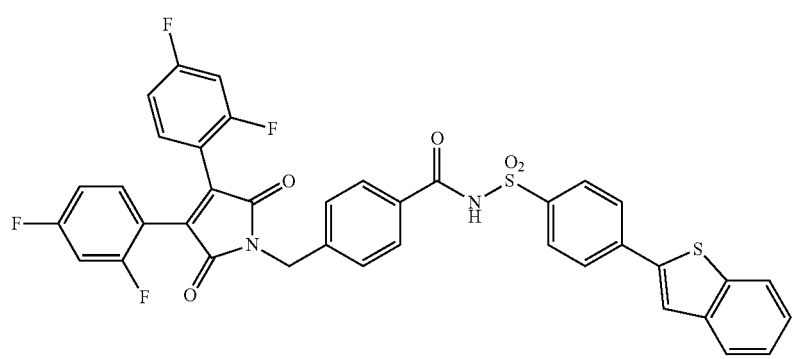
C₃₈H₂₂F₄N₂O₅S₂

-continued
SZ4TA17
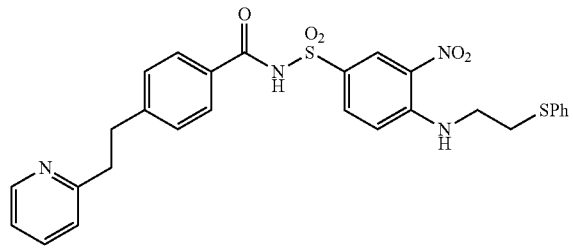
C$_{28}$H$_{26}$N$_4$O$_5$S$_2$
SZ4TA21
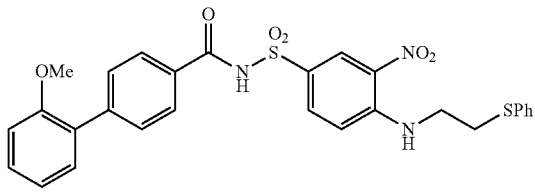
C$_{28}$H$_{25}$N$_3$O$_6$S$_2$
SZ4TA30
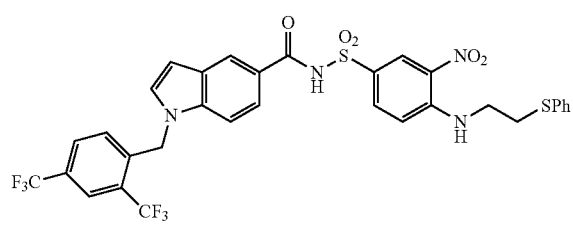
C$_{32}$H$_{24}$F$_6$N$_4$O$_5$S$_2$
SZ6TA23
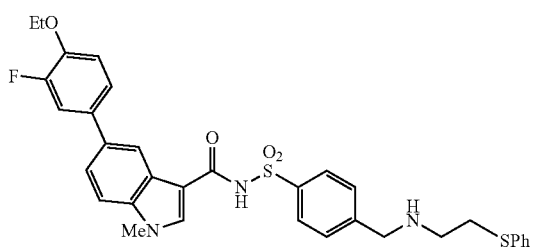
C$_{33}$H$_{32}$FN$_3$O$_4$S$_2$
SZ7TA2
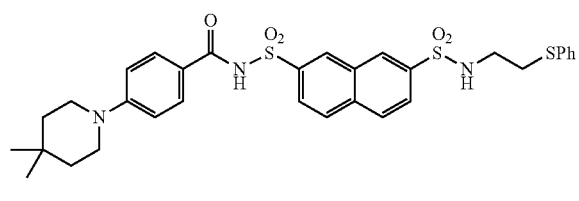
C$_{32}$H$_{35}$FN$_3$O$_5$S$_3$
SZ7TA23
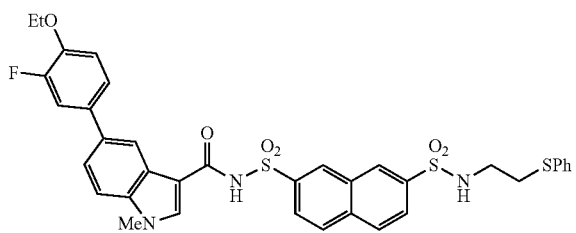
C$_{36}$H$_{32}$FN$_3$O$_5$S$_3$
SZ7TA45
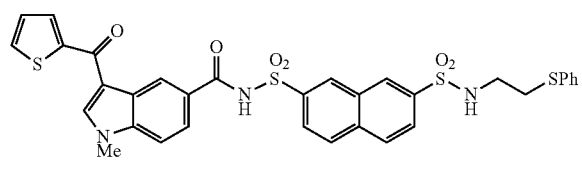
C$_{33}$H$_{27}$N$_3$O$_6$S$_4$
SZ8TA14
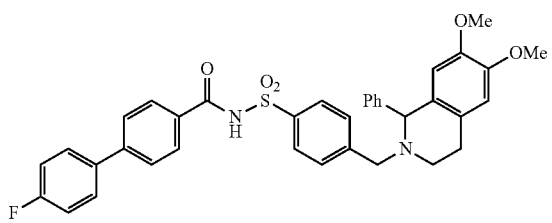
SZ8TA2
C$_{38}$H$_{43}$N$_3$O$_5$S -continued
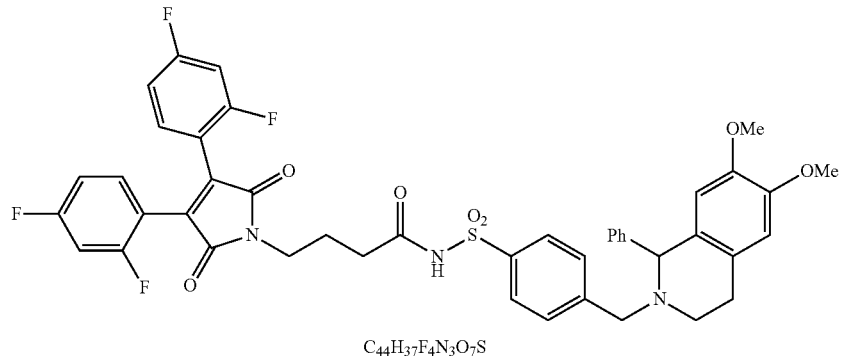
SZ8TA20
C₄₄H₃₇F₄N₃O₇S
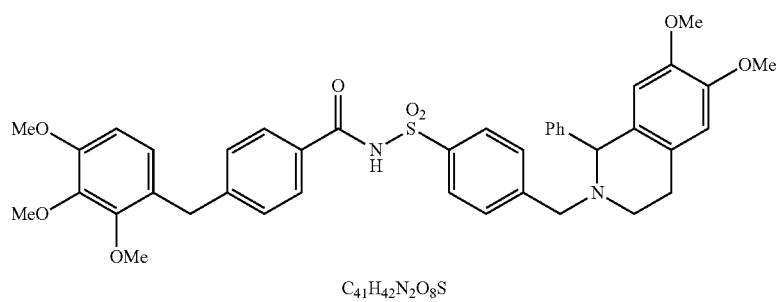
SZ8TA24
C₄₁H₄₂N₂O₈S
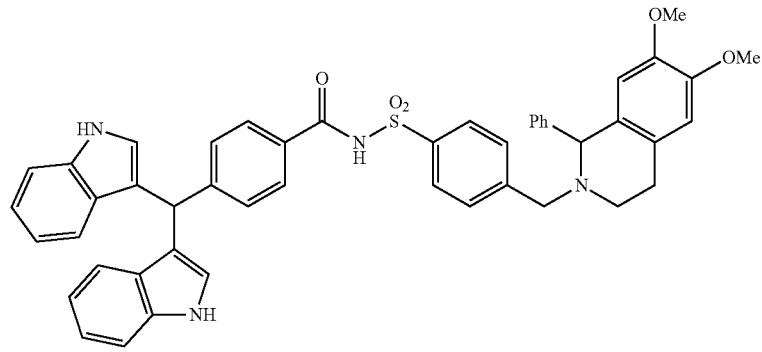
SZ8TA31
C₄₈H₄₂N₄O₅S
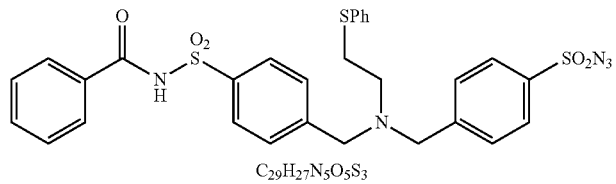
SZ9TA1
C₂₉H₂₇N₅O₅S₃
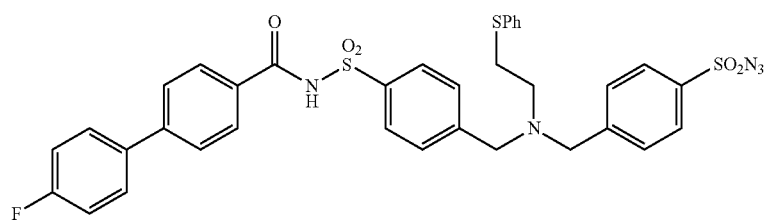
SZ9TA14
C₃₅H₃₀FN₅O₅S₃

-continued

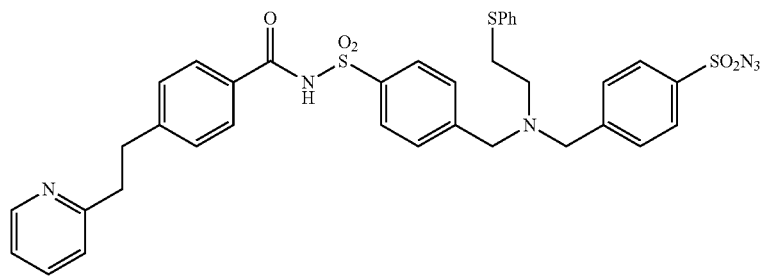
SZ9TA17
$C_{36}H_{34}N_6O_5S_3$

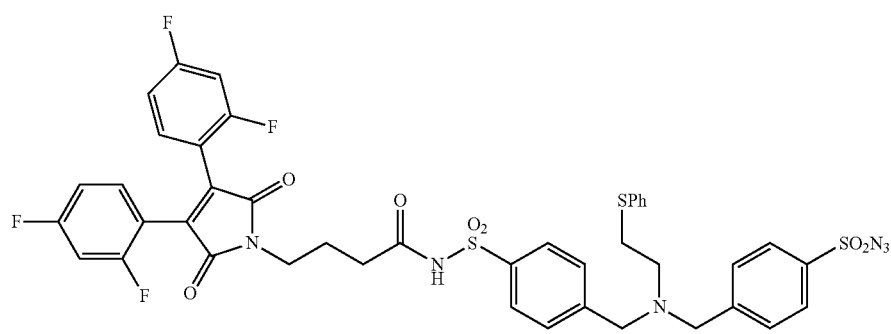
SZ9TA20
$C_{42}H_{34}F_4N_5O_7S_3$

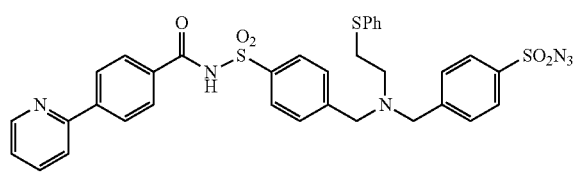
SZ9TA25
$C_{34}H_{30}N_6O_5S_3$

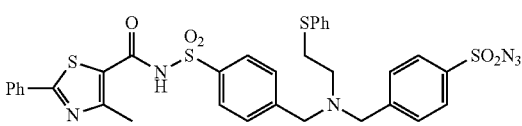
SZ9TA3
$C_{33}H_{30}N_6O_5S_4$

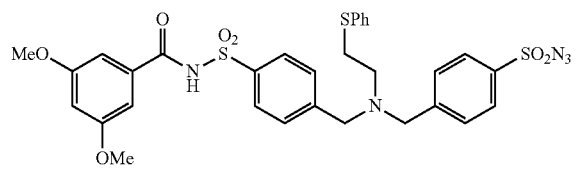
SZ9TA5
$C_{31}H_{31}N_5O_7S_3$

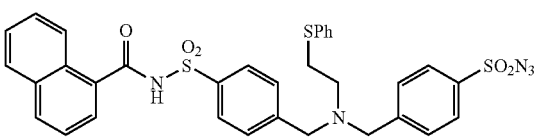
SZ9TA7
$C_{33}H_{29}N_5O_5S_3$

III. Methods of Using Target-Binding Molecules

The target binding molecules can be used to inhibit the function of the target, to alter the function or activity of the target, or to interfere with the binding of the target to another molecule such as a protein or nucleic acid. The target binding molecules or pharmaceutical formulations thereof can be administered to a patient in need thereof to treat or prevent a disease or disorder.

A. Methods of Making Target Binding Molecules

The target binding molecules, one identified by the methods described herein, can be readily synthesized by a variety of methods known to those skilled in the art. The target binding molecules can be synthesized by reacting the fragments from the plurality of fragments that were combined to form the target binding molecule.

In some embodiments the target binding molecule is prepared via an amidation reaction between a thioester and a sulfonyl azide with 1,8-Diazabicyclo[5.4.0]undec-7-ene (DBU). This reaction has the benefit that it can be readily performed at 20-30 mg scale. The 9-fluorenylmethyl thioester can be placed in a 2.0 mL vial and 3.5% DBU/dry DMF solution can be added. Then the sulfonylazide (1 eq to thioester) can be added to the reaction mixture. After the reaction is completed (approximately one minute) water (200 μL) can be added and the pH can be adjusted to 7.0. The reaction mixture can be extracted with DCM until there is no product in the aqueous layer (checked by TLC or LC-MS). The product can be purified by flash chromatography.

B. Pharmaceutical Formulations

Pharmaceutical formulations are provided that contain an effective amount of a target binding molecule in a pharmaceutical carrier appropriate for administration to an individual in need thereof. The formulations can be administered parenterally (e.g., by injection or infusion), topically (e.g., to the eye), or via pulmonary administration.

Parenteral Formulations

The target binding molecule can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the target binding molecule can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the target binding molecule.

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the target binding molecule in the required amount in the appropriate solvent or dispersion medium with one or more of the excipients listed above, as required, followed by filtered sterilization. Generally, dispersions are prepared by incorporating the various target binding molecules into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the target binding molecule plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration are preferably in the form of a sterile aqueous solution or suspension of target binding molecules. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for parenteral administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for parenteral administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration may also contain one or more excipients known art, such as dispersing agents, wetting agents, and suspending agents.

Topical Formulations

The target binding molecule can be formulated for topical administration. Suitable dosage forms for topical administration include creams, ointments, salves, sprays, gels, lotions, emulsions, liquids, and transdermal patches. The formulation may be formulated for transmucosal, transepithelial, transendothelial, or transdermal administration. The compositions contain one or more chemical penetration enhancers, membrane permeability agents, membrane transport agents, emollients, surfactants, stabilizers, and combination thereof.

In some embodiments, the target binding molecule can be administered as a liquid formulation, such as a solution or suspension, a semi-solid formulation, such as a lotion or ointment, or a solid formulation. In some embodiments, the target binding molecules are formulated as liquids, including solutions and suspensions, such as eye drops or as a semi-solid formulation, such as ointment or lotion for topical application to the skin, to the mucosa, such as the eye or vaginally or rectally.

The formulation may contain one or more excipients, such as emollients, surfactants, emulsifiers, penetration enhancers, and the like.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase can contain a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of the conjugates in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams can include an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, it may be desirable to provide continuous delivery of one or more target binding molecules to a patient in need thereof. For topical applications, repeated application can be done or a patch can be used to provide continuous administration of the target binding molecule over an extended period of time.

Enteral Formulations

The target binding molecules can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition which may include plasticizers, pigments, colorants, stabilizing agents, and glidants.

Formulations can be prepared using one or more pharmaceutically acceptable excipients, including diluents, preservatives, binders, lubricants, disintegrators, swelling agents, fillers, stabilizers, and combinations thereof.

Delayed release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The target binding molecule may be coated, for example to delay release once the particles have passed through the acidic environment of the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers and/or pH dependent polymers, with or without water insoluble/water soluble non polymeric excipient, to produce the desired release profile. The coating is either performed on dosage form (matrix or simple) which includes, but not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

C. Methods of Using Target Binding Molecules and Formulations Thereof

As shown in the Examples below, the kinetic TGS approach described herein was used in the screening of 2000 fragment combinations against Bcl-xL and Mcl-1 proteins. The kinetic TGS screening lead to the identification of selective modulators of Bcl-xL, selective modulators of Mcl-1, as well as modulators of Bcl-xL and Mcl-1. The identified compounds were assessed in biochemical assays indicating that these have potential to be developed into viable leads targeting the Bcl-2 family.

It is believed that the kinetic TGS approach provided herein also has the potential to intercept and stabilize short-lived conformations of the protein target by the compounds assembled within the protein target. This kinetic TGS approach to lead discovery will help medicinal chemists by providing a dynamic search method for tracking and intercepting the dynamic protein targets.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

General Protocols

All reagents and solvents were purchased from commercial sources and used without further purification. Column chromatography was carried out using Merck Kieselgel 60 H silica gel. $^1$H NMR, $^{13}$C NMR were recorded on a Bruker 250 MHz and Varian 400 MHz NMR spectrometer. All $^1$H NMR experiments were reported in δ units, parts per million (ppm) downfield of TMS and were measured relative to the signals for chloroform (7.26 ppm) and deuterated methanol (3.35, 4.78 ppm). All $^{13}$C NMR spectra were reported in ppm relative to the signals for chloroform (77 ppm). The HRMS data were measured on an Agilent 1100 Series MSD/TOF with electrospray ionization. The LC/MS data were measured on Thermo Scientific TSQ 8000 Triple Quadrupole LC/MS or an Agilent Technology 6460 Triple Quad LC/MS, using a Phenomenex column Kinetex 2.6 μm PFP, 4.60 mm×50 mm. The elution gradient employed for TQMS-MRM analysis is shown below:

TABLE 1

Elution gradient employed for TQMS-MRM analysis

| Time | % B* | Flow rate |
| --- | --- | --- |
| 0.00 | 10.0 | 0.7 mL min$^{-1}$ |
| 2.00 | 10.0 | 0.7 mL min$^{-1}$ |
| 15.00 | 95 | 0.7 mL min$^{-1}$ |
| 17.00 | 10 | 0.7 mL min$^{-1}$ |

*eluent A: H$_2$O (0.05% TFA); eluent B: CH$_3$CN (0.05% TFA)

Example 2

General Protocol for Multi-Fragment "Sulfo-Click" Kinetic TGS Experiments with Mcl-1 and Bcl-X$_L$ 2 mM stock solutions of the required sulfonyl azide building blocks in methanol was prepared in advance and 100 μL of each stock solution was combined in a via (using all sulfonyl azides needed for the multi-fragment incubation). The solvent was evaporated and 100 μL fresh MeOH was added in the vial in order to obtain multi-component mixture of sulfonyl azides with 2 mM final concentration of each sulfonyl azide. Each thio acid used for the multi-fragment screening was prepared by individually de-protecting the corresponding fluorenylmethyl thioesters (~500 μg weighted in a 2 mL eppendorf) with 5% piperidine in DMF for 2-4 min (1 μL solution used for 4.7 μmol thioester) and each reaction was diluted with methanol in order to generate 20 mM stock solution of the corresponding thio acid. The thio acids required for the multi-component screening were combined in an eppendorf vial and further diluted with methanol to 2 mM final solution of each thioacid. In a 96-well plate, 1 μL of the prepared multi-component solution of thio acid mixture and 1 μL of the prepared multi-component sulfonyl azide mixture were added to a solution of Mcl-1 (98 μL of 10 μM Mcl-1 solution in buffer) or to the solution of Bcl-X$_L$ (98 μL of 10 μM Bcl-X$_L$ solution in buffer). The phosphate buffer used for the incubations (pH=7.40) has the following composition: 58 mM Na$_2$HPO$_4$, 17 mM NaH$_2$PO$_4$, 68 mM NaCl, 1 mM NaN$_3$. In addition to that, a set of incubation was carried out under the same conditions but in the presence of buffer only (background reaction). The 96-well plate was incubated at 37° C. for twelve hours. The incubation mixtures were then subjected to Liquid Chromatography combined with triple quadrupole mass spectrometry in the Multiple Reaction Monitoring mode (MRM), equipped with Kinetex PFP column (4.60 mm×50 mm) proceeded by a Phenomenex C18 guard column. The injection volume was 20 μL at a flow rate of 0.7 mL/min (see Table 1).

Example 3

Parallel Sulfo-Click Kinetic TGS Screening of Multiple Protein-Protein Interactions: Advantages of the Use of MS/MS Instrumentation in Kinetic TGS Obstacles of conventional kinetic TGS due to the instrumental limitations could be overcome by a screening using a more advanced mass spectrometry technology. For example, the triple quadrupole mass spectrometry (TQMS) is a proven technique with numerous advantages offering superior sensitivity over the single quadrupole instrumentation. TQMS offers a better signal-to-noise ratio (S/N), resulting in a significantly lower limit of detection and quantitation. Moreover, the analysis with this highly sensitive technology allows for a simultaneous detection of several targeted reactions by using a Multiple Reaction Monitoring (MRM) mode as opposed to Selected Ion Mode (SIM). In comparison to the full-mass scan (FIG. 1.A), the SIM mode (FIG. 1.B) provides higher sensitivity due to a longer instrument dwells time on a narrower mass range with a pre-set m/z ratio of a precursor ion. However, in the MRM experiment (FIG. 1.C), in addition to the pre-set precursor ion, a unique fragment ion is delivered which can be easily monitored to provide quantified analysis of more complex mixtures. Moreover, unlike the MRM mode, the SIM mode can not be used to analyze reaction mixtures of compounds which have the same m/z ratio. The MRM mode can easily distinguish between the same m/z ratio of precursor ion as they would generate different fragment ions, distinct for each compound. The high reproducibility and better accuracy obtained even at low analyte concentrations are other beneficial features of TQMS in the MRM scan mode.

Conceivably, employing the sulfo-click multi-fragment screening approach, coupled with triple quadrupole mass spectrometry, is an opportunity to improve the throughput and to take the kinetic TGS to its next level of efficiency and productivity. Such a multi-component screening strategy has the potential to drastically increase the number of screened reactions, to reduce the time used for preparation of a single sulfo-click reaction, and to also cut down the amount of the consumed proteins and reagents. By using a triple-quadrupole mass spectrometer, it was demonstrated that acylsulfonamide products can be reliably detected in incubation samples containing 200 or more fragment combinations in one single well. The simultaneous incubation of 2-300 fragment combinations (a) increases the screening time efficiency by about ~2-300-times, (b) ensures a 15- to 20-fold improvement of sample/reagents economy, c) cuts down the time required for the preparation of each incubation reaction by about 2-300-times; d) ensures better hit detectability by utilizing the enhanced multi-reaction-monitoring mode of sample detections.

Example 4

Figure 2:
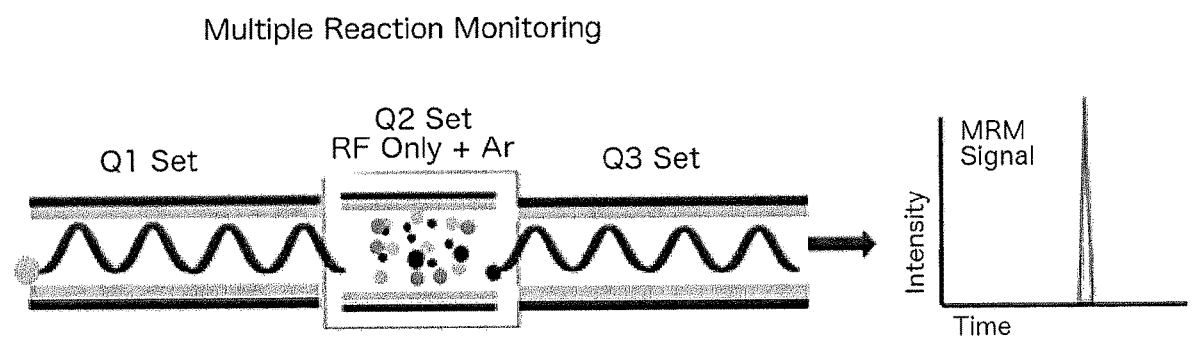
FIG. 2 is a schematic representation of Multiple Reaction Monitoring (MRM) mode of analysis performed with a triple quadrupole mass spectrometer.

Optimization of Multi-Fragment Sulfo-Click Kinetic TGS Screening with Triple Quadrupole Mass Spectrometry Detection For quantitative analysis, the improved sensitivity offered by the triple quadrupole mass technology or any tandem mass spectrometry instruments (MS/MS instruments) is further enhanced by utilizing the instrument in the multiple reaction monitoring mode (MRM). Examples of instrumentation with tandem mass spectrometry capabilities are ion traps, Q-traps. Orbitraps, Q-TOFs, and others. The MRM mode significantly improves the quality of the detected signal by serving as a 'double filter' which allows only a pre-set precursor ion with a specified product ion to pass through the three quadrupoles ultimately reaching the mass analyzer (FIG. 2). For example, a quadrupole mass analyzer is comprised of four parallel rods in which fixed DC and alternating RF potentials are applied. The first filtering process is conducted within the first quadrupole wherein only a precursor ion with a pre-set mass to charge ratio (m/z) has a stable trajectory reaching the second quadrupole (Q2). In the second quadrupole, the precursor ion is collisionally fragmented into a characteristic product ion, which passes the third quadrupole (Q3) and reaches the mass analyzer, only if its m/z ratio corresponds to the specifically defined m/z settings of the third quadrupole. All other product ions that do not resonate with the specific DC/RF voltage combination will be filtered out in the third quadrupole. Thus, this advanced engineering design coupled with an MRM screening mode reduces the noise level, and increases the selectivity and sensitivity of the analysis.

As described above, utilizing the MRM method requires knowledge of not only the m/z ratio of the precursor ion of interest but also that of the corresponding product ion generated at particular collision energy (eV). In order to correlate the collision energies to fragmentation pathways, a direct infusion experiment was performed in which a methanolic solution of an acylsulfonamide was injected into the collision cell, providing information of the fragmentation patterns at corresponding collision energies (example of acylsulfonamide SZ8TA4 is presented on FIG. 3). From this particular experiment and the several others performed with various acylsulfonamides (SZ1TA3, SZ2TA2, SZ7TA2, SZ2TA4, SZ9TA7, SZ7TA7, SZ6TA7, SZ9TA1, and SZ8TA8), it was concluded that among all tested acylsulfonamides there was a common similarity in the collision-activated breaking of the acylsulfonamide linkage. It was observed that the acylium ion was present in all investigated acylsulfonamides, and that this particular product ion was often the most abundant species among all other fragments.

The intensity of each defragmentation curve corresponds to the abundance of a particular product ion at that collision energy, relative to the amount of the rest of fragments generated at the defragmentation process. The relative abundance of each ion is determined by the number of times an ion of particular m/z ratio strikes the detector. The average collision energy corresponding to the formation of the acylium ion for all the tested acylsulfonamides was determined to be between 30-35 V (Table 2), which was extrapolated to the rest of the entire acylsulfonamide library which were not tested individually.

The fragmentation pathway leading to the acylium ion was advantageous to establish a practical way to set up and analyze multi-component incubation samples. The instrument sensitivity and the data analysis of multi-component kinetic TGS screening samples containing a smaller number of thio acid fragments and a larger number of sulfonyl azides are better and easier in comparison to an incubation sample containing a larger number of thio acid fragments and a smaller number of sulfonyl azides. If several acylsulfonamides generated from the same thio acid will be kept in the same kinetic TGS screening sample, they all commonly generate the identical acylium ion as the product ion. In contrast, an incubation sample containing acylsulfonamides structurally differing in their carbonyl moieties, MRM will generate a multitude of acylium ions, which decreases the overall sensitivity of the instrument and increases the complexity of the raw data analysis.

Example 5

Proof-of-Concept Studies Targeting the Proteins of the Bcl-2 Family

In a proof-of-concept study based on a previous kinetic TGS study targeting Bcl-$X_L$, it was demonstrated that a multi-fragment kinetic TGS approach coupled with TQMS technology was successfully implemented in the identification of known protein-protein modulators. Optimized screening conditions utilizing a triple quadruple mass spectrometer or any other MS/MS 75 instrumentation in the Multiple Reaction Monitoring (MRM) mode was proven to be very efficient in kinetic TGS hit identification increasing both the throughput and the sensitivity of this approach. The multi-fragment incubation approach was studied in detail and it was concluded that 2-300 fragment combinations in one well are feasible and practical numbers permitting good acylsulfonamide detectability. Overall, the presented multi-component kinetic TGS technique has shown to have a great potential in streamlining the kinetic screening method as well as accelerating the hit identification process. Importantly, this multi-fragment kinetic TGS screening is generally applicable and it has the potential to be utilized for the screening of any biological targets such as protein-protein interaction targets or protein-DNA/RNA interactions.

In a subsequent study, a structurally diverse library of forty five thio acids and thirty eight sulfonyl azides (identified above) was screened in parallel against Mcl-1 and Bcl-$X_L$ using the above mentioned approach. Several potential hit combinations were identified (Table 3). All of these kinetic TGS hit compounds were synthesized (identified above and in Table 3). All the reactions were performed at 20-30 mg scale. The 9-fluorenylmethyl thioester was placed in a 2.0 mL vial and 3.5% DBU/dry DMF solution was added (per 1 μmol of thioester, 4.7 μL, of 3.5% DBU/dry DMF solution was added) and the reaction was stirred for one minute. Then the sulfonylazide (1 eq to thioester) was added to the reaction mixture and immediately bubbling was observed. After the reaction was completed (approximately one minute, monitored by LC-MS) water (200 μL) was added and the pH was adjusted to 7.0 using 1M HCl solution. The reaction mixture was extracted with DCM until there is no product in the aqueous layer (checked by TLC or LC-MS). The product was purified by flash chromatography. Testing of these acylsulfonamides has shown that the hit compounds disrupt the Bcl-$X_L$/Bim or Mcl-1/Bim interaction (Table 3).

TABLE 2

Collision energy (eV) at which the corresponding acylium ion is generated through the defragmentation process

| Acylsulfonamide | Collision energy (eV) required to generate the acylium ion |
|---|---|
| SZ1TA3 | 29 |
| SZ2TA2 | 26 |

TABLE 2-continued

Collision energy (eV) at which the corresponding acylium ion is generated through the defragmentation process

| Acylsulfonamide | Collision energy (eV) required to generate the acylium ion |
|---|---|
| SZ7TA2 | 28 |
| SZ2TA4 | 22 |
| SZ8TA4 | 26 |
| SZ9TA7 | 37 |
| SZ7TA7 | 31 |
| SZ6TA7 | 31 |
| SZ9TA1 | 48 |
| SZ8TA8 | 36 |

TABLE 3

Inhibition of Mcl-1 and Bcl-$X_L$ (% inhibition) at 50 µM and 25 µM and the corresponding $IC_{50}$ values (µM) for several acylsulfonamides identified by kinetic TGS.

| | Compound Identifier | Mcl-1 | | Bcl-$X_L$ | | $IC_{50}$ | |
|---|---|---|---|---|---|---|---|
| | | % Inhibition (50 µM) Mcl-1 | % Inhibition (25 µM) Mcl-1 | % Inhibition (50 µM) Bcl-$X_L$ | % Inhibition (25 µM) Bcl-$X_L$ | Bcl-$X_L$ | Mcl-1 |
| 1 | SZ10TA15 | 37.4 | 35.2 | <2.0 | 9.4 | | |
| 2 | SZ10TA2 | 94.7 | 41.7 | 52.1 | | 44 µM | 15.8 µM |
| 3 | SZ10TA20 | 7.6 | 27.8 | <2.0 | 3.8 | | |
| 4 | SZ10TA21 | 57.3 | 52.3 | | | | |
| 5 | SZ10TA25 | 93.6 | 43.9 | 53.4 | 33.9 | | |
| 6 | SZ10TA34 | 64.1 | 19.4 | 27.0 | 17.4 | | |
| 7 | SZ10TA40 | 35.2 | 37.2 | <2.0 | <2.0 | | |
| 8 | SZ10TA41 | 12.4 | 2.8 | | | | |
| 9 | SZ10TA44 | 63.4 | 27.6 | 20.6 | 9.9 | | |
| 10 | SZ11TA25 | 65.8 | 20.1 | | | | |
| 11 | SZ11TA30 | 63.6 | 53.1 | <2.0 | 8.5 | | |
| 12 | SZ11TA40 | >99.0 | 74 | 58.7 | 30.7 | | 21.9 µM |
| 13 | SZ12TA2 | 54.1 | 7.1 | | | | |
| 14 | SZ12TA23 | 21.5 | 6.1 | | | | |
| 15 | SZ12TA42 | 89.4 | 77.3 | 22.6 | 14.0 | | 13.6 µM |
| 16 | SZ14TA40 | 93.1 | 68.5 | 47.9 | 27.8 | | |
| 17 | SZ14TA42 | 46.0 | 46.5 | <2.0 | <2.0 | | |
| 18 | SZ15TA1 | 92.5 | | 53.4 | | 29.1 µM | 9.7 µM |
| 19 | SZ15TA14 | 58.8 | 65.8 | 23.2 | 31.1 | | |
| 20 | SZ15TA15 | 53.6 | 42.2 | 8.8 | 10.1 | | |
| 21 | SZ15TA17 | 89.5 | 79.6 | 60.0 | 43.4 | 55.9 µM | 20.2 µM |
| 22 | SZ15TA24 | 70.8 | 54.4 | 18.9 | 14.7 | | |
| 23 | SZ15TA25 | 89.0 | 77.2 | 57.8 | 43.0 | 54.9 µM | 15.3 µM |
| 24 | SZ15TA3 | 95.9 | | 43 | | 36.4 µM | 5.8 µM |
| 25 | SZ15TA34 | 82.8 | 47.4 | 28.6 | 19.6 | | |
| 26 | SZ15TA5 | >99.0 | | 38.4 | | 53 µM | 13.4 µM |
| 27 | SZ15TA7 | 98.4 | | | | | 15.4 µM |
| 28 | SZ15TA8 | 96.5 | <2.0 | 12.4 | 3.4 | 47 µM | 7.6 µM |
| 29 | SZ16TA21 | 80.9 | 26.0 | | | | |
| 30 | SZ16TA44 | 98.1 | 49.9 | 55.5 | 26.8 | | 31.5 µM |
| 31 | SZ17TA14 | 46.7 | 73.9 | 2.8 | 16.6 | | |
| 32 | SZ17TA15 | 60.6 | 53.3 | 12.0 | 3.0 | | |
| 33 | SZ17TA17 | 89.0 | 73.9 | 58.4 | 68.1 | | |
| 34 | SZ17TA20 | 12.4 | 7.2 | <2.0 | <2.0 | | |
| 35 | SZ17TA24 | 74.1 | 65.1 | | | | |
| 36 | SZ17TA25 | 93.6 | 64.9 | 54.5 | 38.6 | | |
| 37 | SZ17TA3 | 100 | | 39.6 | | 50 µM | 8.6 µM |
| 38 | SZ17TA30 | 15.8 | 18.0 | <2.0 | <2.0 | | |
| 39 | SZ17TA40 | 58.5 | 25.8 | <2.0 | 7.5 | | |
| 40 | SZ17TA45 | 34.5 | 62.7 | <2.0 | 6.8 | | |
| 41 | SZ17TA7 | 87.3 | | 66.5 | | 72 µM | 20.1 µM |
| 42 | SZ17TA8 | 100 | 60.45 | <2.0 | 4.1 | | 8.4 µM |
| 43 | SZ1TA14 | 24.4 | 9.0 | <2.0 | 9.6 | | |
| 44 | SZ1TA23 | 21.5 | 18.7 | | | | |
| 45 | SZ1TA30 | 2.6 | 11.8 | <2.0 | <2.0 | | |
| 46 | SZ21TA23 | 42.8 | 9.7 | | | | |
| 47 | SZ23TA2 | <2.0 | 4.5 | | | | |

TABLE 3-continued

Inhibition of Mcl-1 and Bcl-X$_L$ (% inhibition) at 50 μM and 25 μM and the corresponding IC$_{50}$ values (μM) for several acylsulfonamides identified by kinetic TGS.

| | | Mcl-1 | | Bcl-X$_L$ | | IC$_{50}$ | |
|---|---|---|---|---|---|---|---|
| | Compound Identifier | % Inhibition (50 μM) Mcl-1 | % Inhibition (25 μM) Mcl-1 | % Inhibition (50 μM) Bcl-X$_L$ | % Inhibition (25 μM) Bcl-X$_L$ | Bcl-X$_L$ | Mcl-1 |
| 48 | SZ24TA30 | 11.4 | 18.1 | | | | |
| 49 | SZ27TA42 | 52.3 | 18.3 | 5.2 | 14.1 | | |
| 50 | SZ28TA30 | 60.5 | 42.8 | <2.0 | 9.7 | | |
| 51 | SZ28TA31 | 25.8 | 22.6 | <2.0 | 8.1 | | |
| 52 | SZ28TA45 | 54.0 | 46.8 | 34.6 | 25.7 | | |
| 53 | SZ2TA31 | 16.2 | 14.2 | 9.4 | 14.9 | | |
| 54 | SZ31TA14 | 59.5 | 56.2 | 13.3 | 17.3 | | |
| 55 | SZ31TA15 | 80.7 | 82.0 | 21.4 | 18.5 | | 14.0 μM |
| 56 | SZ31TA17 | 88.6 | 84.3 | 77.7 | 40.2 | 31.3 μM | 16.8 μM |
| 57 | SZ31TA24 | 82.4 | 59.9 | 15.5 | 8.2 | | 20.0 μM |
| 58 | SZ31TA3 | 100 | 69.89 | 51.3 | 29.6 | | 9.4 μM |
| 59 | SZ31TA30 | 30.6 | 32.4 | <2.0 | <2.0 | | |
| 60 | SZ31TA31 | <2.0 | <2.0 | <2.0 | <2.0 | | |
| 61 | SZ31TA40 | <2.0 | <2.0 | <2.0 | <2.0 | | |
| 62 | SZ31TA44 | 36.5 | 14.9 | <2.0 | <2.0 | | |
| 63 | SZ31TA45 | 40.2 | 53.8 | <2.0 | 7.2 | | |
| 64 | SZ31TA8 | >99.0 | 61.2 | | 9.5 | | 5.9 μM |
| 65 | SZ32TA42 | 91.0 | 72.2 | 59.4 | 26.0 | 43.8 μM | 19.1 μM |
| 66 | SZ34TA42 | >99.0 | 49.0 | 58.0 | 19.1 | | 29.3 μM |
| 67 | SZ35TA17 | 89.2 | 18.8 | | | | |
| 68 | SZ35TA24 | 76.4 | 72.3 | | | | |
| 69 | SZ35TA3 | 87.2 | 18.8 | | | | |
| 70 | SZ35TA7 | 87.8 | 28.6 | | | | |
| 71 | SZ36TA2 | 48.7 | 10.5 | | | | |
| 72 | SZ37TA42 | 22.7 | <2.0 | <2.0 | 21.8 | | |
| 73 | SZATA17 | 44.7 | 30.8 | 90.6 | 83.7 | 2.08 μM | 60.6 μM |
| 74 | SZ4TA21 | 80.6 | 44.7 | | | | |
| 75 | SZ4TA30 | 80.7 | 68.7 | 42.6 | 41.2 | >50 μM | 26.1 μM |
| 76 | SZ6TA23 | <2.0 | <2.0 | | | | |
| 77 | SZ7TA2 | 93.9 | 49.6 | 73.0 | 15.5 | 28.6 μM | 16.9 μM |
| 78 | SZ7TA23 | 7.9 | 6.1 | | | | |
| 79 | SZ7TA45 | 86.7 | 41.0 | | | | |
| 80 | SZ8TA14 | 58.3 | 35.2 | 13.9 | 14.4 | | |
| 81 | SZ8TA2 | 24.9 | 14.8 | | | | |
| 82 | SZ8TA20 | 19.2 | 23.5 | <2.0 | 9.1 | | |
| 83 | SZ8TA24 | 79.2 | 43.6 | | | | |
| 84 | SZ8TA31 | <2.0 | <2.0 | <2.0 | <2.0 | | |
| 85 | SZ9TA1 | 97.3 | | 79.5 | | 28.8 μM | 19.8 μM |
| 86 | SZ9TA14 | 42.5 | 30 | 7.0 | 8.4 | | |
| 87 | SZ9TA17 | 103.3 | 69.3 | 63.5 | 50.0 | | 20.4 μM |
| 88 | SZ9TA20 | 6.9 | 15.7 | <2.0 | <2.0 | | |
| 89 | SZ9TA25 | 47.6 | 43.1 | <2.0 | 18.6 | | |
| 90 | SZ9TA3 | 83.1 | | 21.6 | | | 22.7 μM |
| 91 | SZ9TA5 | >99.0 | 50.0 | 60.3 | 8.6 | 36.0 μM | 8.1 μM |
| 92 | SZ9TA7 | 94.1 | | 44.5 | | 66.3 μM | 8.2 μM |

We claim:

1. A method of identifying a target binding molecule comprising:
providing a plurality of first fragments, wherein the first fragments are thioacids;
providing a plurality of second fragments, wherein the second fragments are sulfonyl azides capable of forming a covalent bond with the first fragments;
combining the first fragments and the second fragments in a mixture with the target;
reacting at least one of the first fragments with at least one of the second fragments to form one or more target binding molecules, wherein the one or more target binding molecules are acylsulfonamides; and
analyzing the mixture with both liquid chromatography and triple quadrupole mass spectrometry to identify a mass spectrometer-mediated fragmentation product and identify a target binding molecule from the one or more target binding molecules corresponding to the fragmentation product, wherein the analyzing step comprises multiple reaction monitoring with a collision energy of about 30 eV to about 35 eV to identify the target binding molecule corresponding to the fragmentation product, wherein the fragmentation product is an acylium ion fragmentation product, and wherein the target is a polypeptide or a polynucleotide.

2. The method of claim 1, wherein the number of different first fragments multiplied by the number of different second fragments is about 200-10,000.

3. The method of claim 1, wherein the target is a Bcl-2 family protein selected from the group consisting of Bcl-2, Bcl-XL, Mcl-1, Mcl-2, A1/BFL-1, Boo/Diva, Bcl-w, Bcl-y, Bak, Bax, Bad, tBid, Harakiri, Bim, Bcl-Xs, Bmf, Egl-1, Puma, and Noxa.

4. The method of claim 1, wherein the first fragment and the second fragment are small molecules.

5. The method of claim 1, wherein at least one of the first fragments or the second fragments is a polypeptide or polynucleotide fragment.

6. The method of claim 1, wherein the number of different first fragments multiplied by the number of different second fragments is at least 100.

* * * * *